US009933339B2

(12) United States Patent
Briggman

(10) Patent No.: US 9,933,339 B2
(45) Date of Patent: Apr. 3, 2018

(54) MINIATURE SERIAL SECTIONING MICROTOME FOR BLOCK-FACE IMAGING

(71) Applicant: The United States of America, as represented by the Secretary, Department of Health and Human Services, Washington, DC (US)

(72) Inventor: Kevin L. Briggman, Gaithersburg, MD (US)

(73) Assignee: The United States of America as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 15/308,522

(22) PCT Filed: May 12, 2015

(86) PCT No.: PCT/US2015/030359
§ 371 (c)(1),
(2) Date: Nov. 2, 2016

(87) PCT Pub. No.: WO2015/175525
PCT Pub. Date: Nov. 19, 2015

(65) Prior Publication Data
US 2017/0067800 A1    Mar. 9, 2017

Related U.S. Application Data

(60) Provisional application No. 61/991,929, filed on May 12, 2014.

(51) Int. Cl.
*G01N 1/06* (2006.01)
*G01N 1/00* (2006.01)
(Continued)

(52) U.S. Cl.
CPC ............. *G01N 1/06* (2013.01); *G01N 23/225* (2013.01); *H01J 37/20* (2013.01); *H01J 37/222* (2013.01);
(Continued)

(58) Field of Classification Search
USPC ........ 83/76.9, 375, 401, 411, 412, 452, 713; 250/491.1, 526
See application file for complete search history.

(56) References Cited

U.S. PATENT DOCUMENTS 3,771,405 A * 11/1973 Blum ....................... G01N 1/06
 83/412
4,377,958 A * 3/1983 Leighton .................. G01N 1/06
 83/410.7
(Continued)

FOREIGN PATENT DOCUMENTS

WO    WO 2013/136260    9/2013

OTHER PUBLICATIONS

Denk et al., "Serial Block-Face Scanning Electron Microscopy to Reconstruct Three-dimensional Tissue Nanostructure," *PLoS Biology*, 2(11):1900-1909 (Nov. 2004).
(Continued)

*Primary Examiner* — Bernard Souw
(74) *Attorney, Agent, or Firm* — Klarquist Sparkman, LLP

(57) ABSTRACT

The present disclosure is directed to embodiments of microtome devices and methods of their use. In some embodiments, a microtome can be mounted on the built-in stage of a scanning electron microscope and used to perform serial block-face scanning electron microscopy. In some cases, a microtome installed in a scanning electron microscope can cut the sample at a location off the electron beam axis of the scanning electron microscope. In some cases, a microtome
(Continued)

can include a capacitive sensor which can measure the location of a blade of the microtome, and the microtome can be computer-controlled by program implemented in MAT-LAB.

32 Claims, 24 Drawing Sheets

(51) Int. Cl.
| | | |
|---|---|---|
| *G01N 1/04* | (2006.01) | |
| *H01J 37/20* | (2006.01) | |
| *H01J 37/22* | (2006.01) | |
| *H01J 37/26* | (2006.01) | |
| *G01N 23/225* | (2018.01) | |
| *H01J 37/28* | (2006.01) | |

(52) U.S. Cl.
CPC .............. *H01J 37/26* (2013.01); *H01J 37/28* (2013.01); *G01N 2001/061* (2013.01); *G01N 2001/066* (2013.01); *H01J 2237/20207* (2013.01); *H01J 2237/20214* (2013.01)

(56) References Cited

U.S. PATENT DOCUMENTS

| | | | | |
|---|---|---|---|---|
| 5,461,953 A | * | 10/1995 | McCormick | ............. G01N 1/06 83/36 |
| 5,752,425 A | * | 5/1998 | Asakura | ................... G01N 1/06 83/412 |
| 6,644,162 B1 | * | 11/2003 | Temple | .................... G01N 1/06 83/698.11 |
| 7,297,947 B2 | * | 11/2007 | Motoi | ...................... G01N 1/32 250/306 |
| 8,104,389 B2 | | 1/2012 | Tanki et al. | |
| 8,746,585 B2 | | 6/2014 | Harwood et al. | |
| 2010/0093022 A1 | | 4/2010 | Hayworth et al. | |
| 2010/0216221 A1 | | 8/2010 | Walter et al. | |
| 2012/0055300 A1 | | 3/2012 | Kong et al. | |
| 2012/0223228 A1 | | 9/2012 | Galloway | |
| 2013/0174301 A1 | | 7/2013 | Robinson | |

OTHER PUBLICATIONS

FEI Company, "Ultra-high resolution characterization and analysis of the widest range of samples, with extreme ease!" Product Data—Nova™ NanoSEM 50 series, 4 pages (Feb. 2011).

International Search Report and Written Opinion for related International Application No. PCT/US2015/030359, dated Aug. 18, 2015, 13 pages.

Studer et al., "Minimal compression of ultrathin sections with use of an oscillating diamond knife," *Journal of Microscopy*, 197(1):94-100 (Jan. 2000).

\* cited by examiner

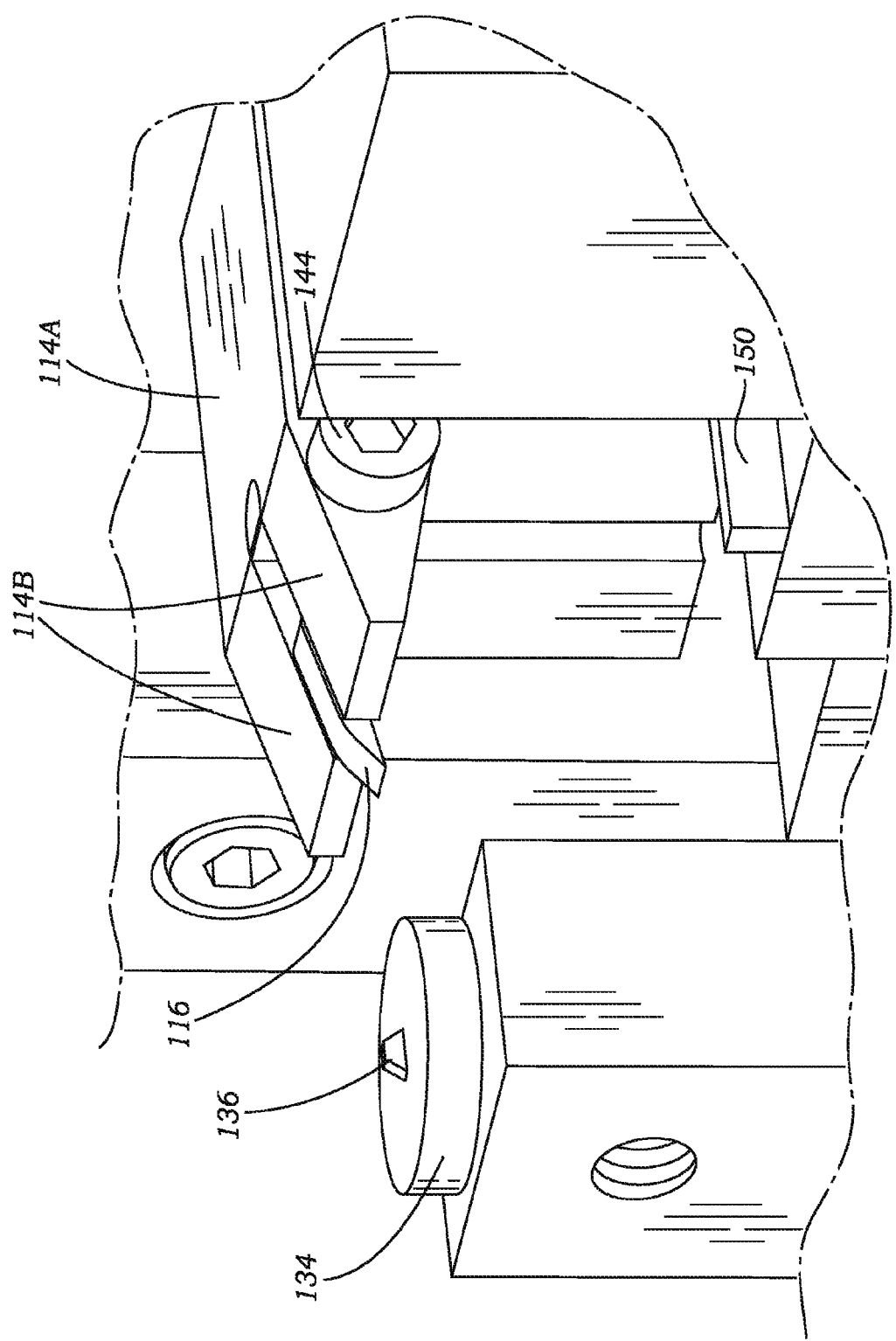

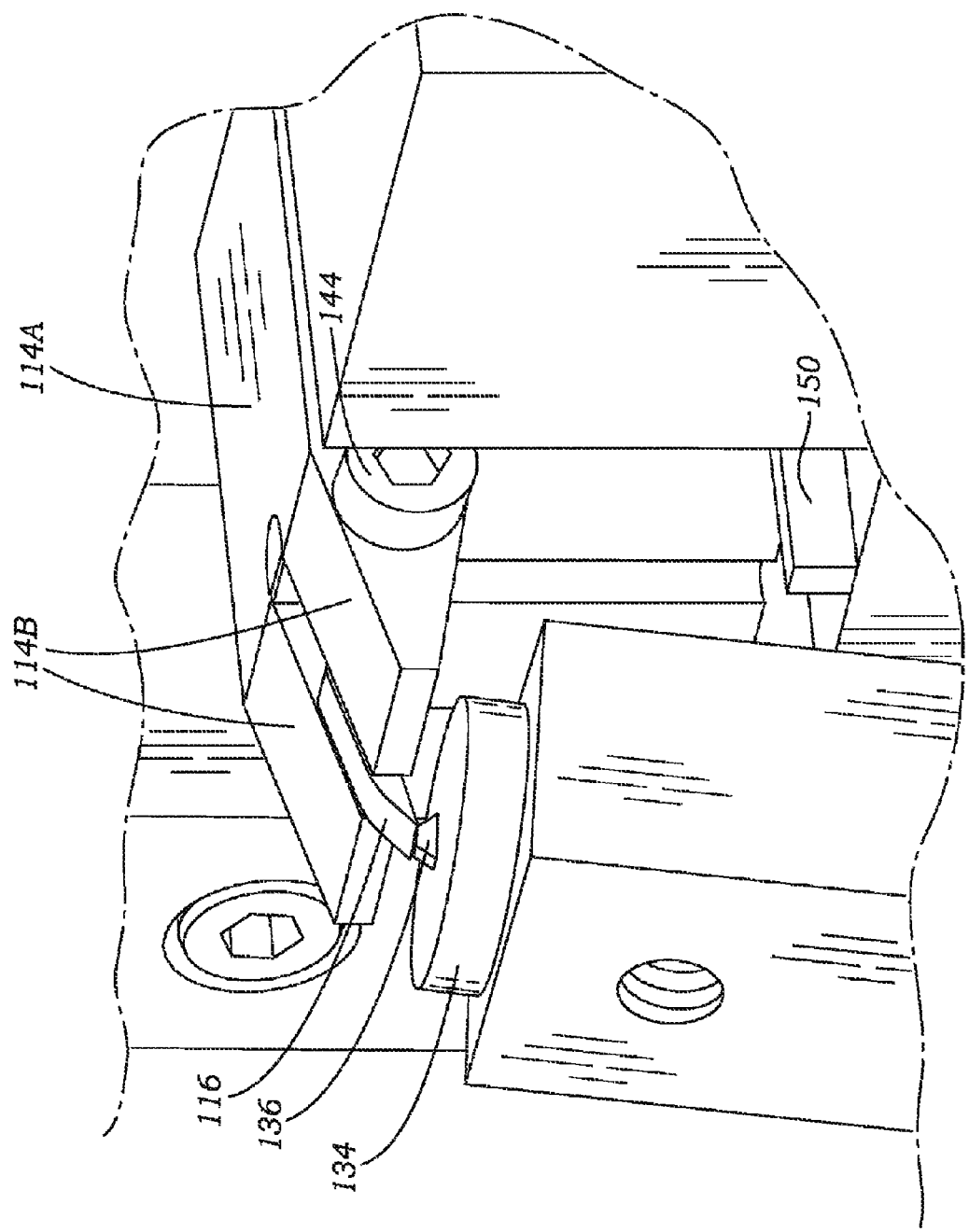

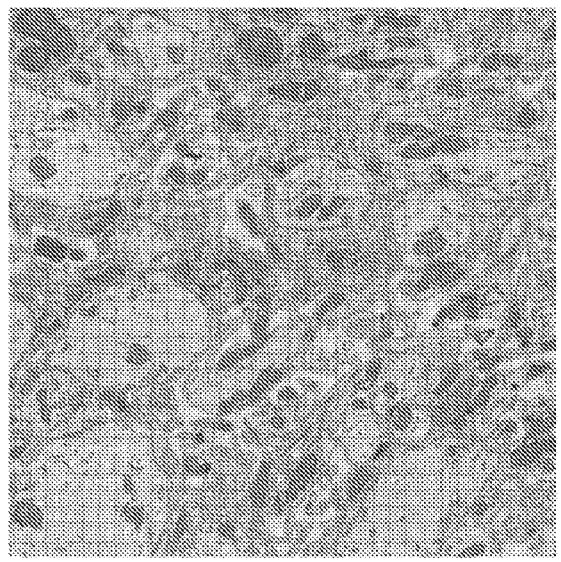 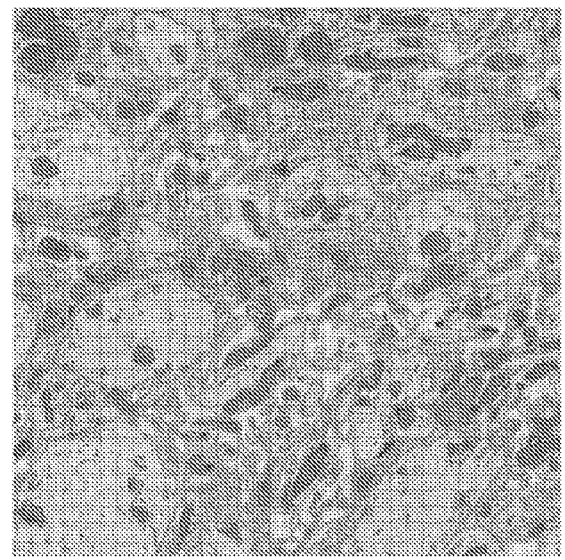
FIG. 3M     FIG. 3N
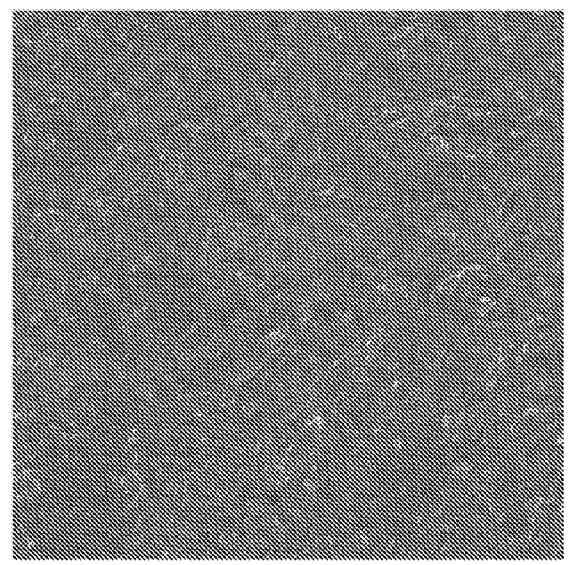
FIG. 3O

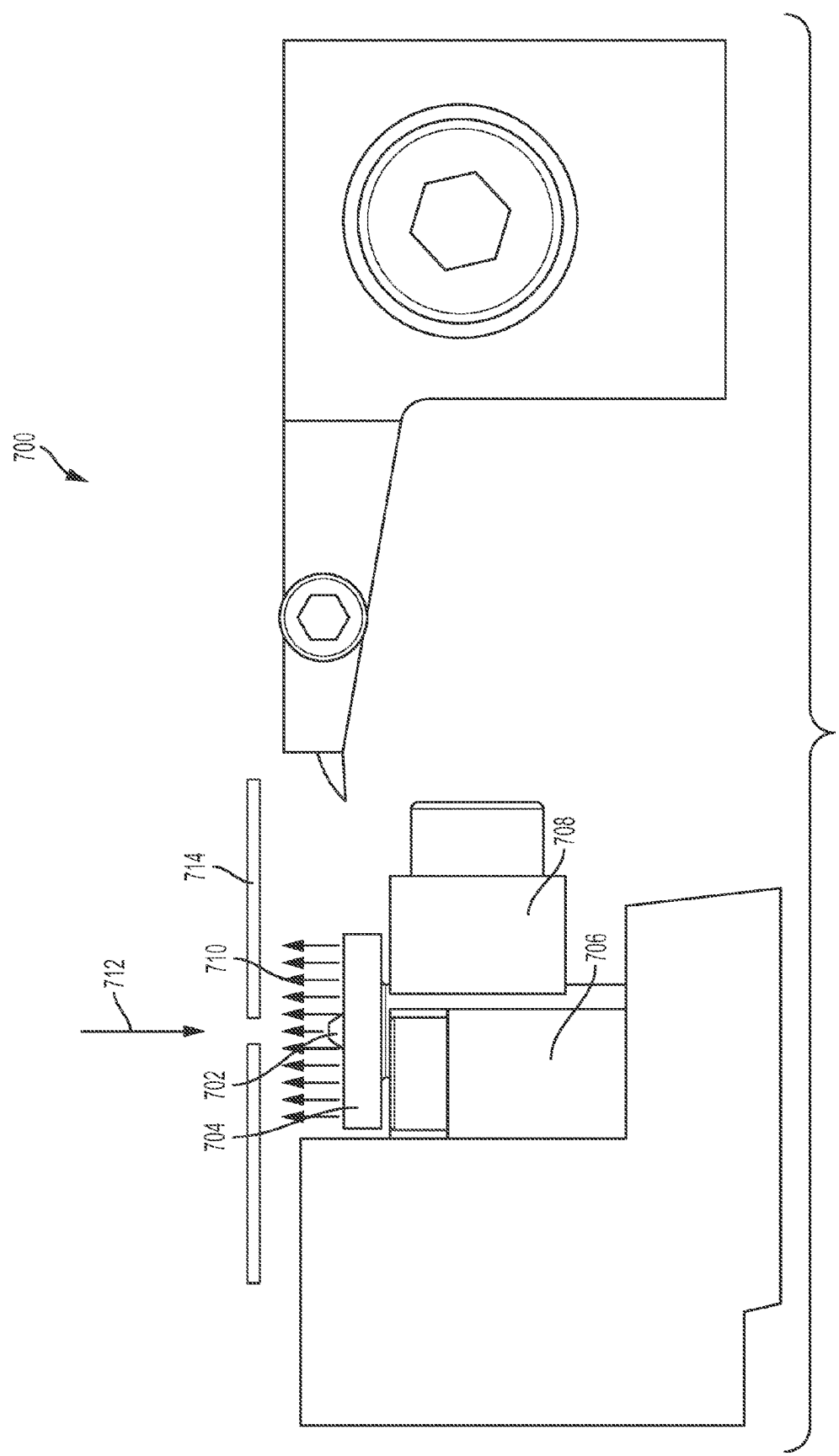

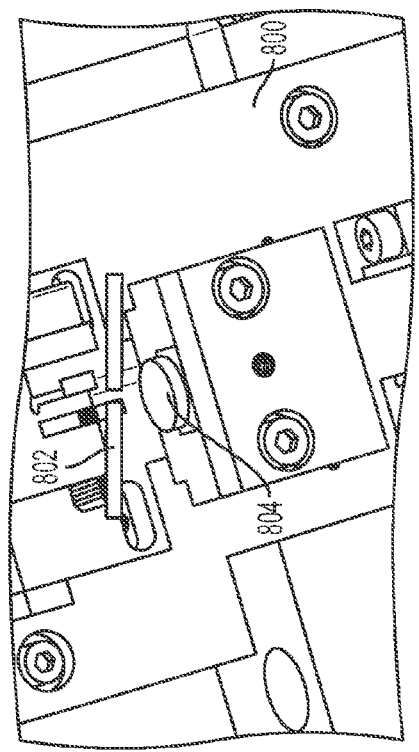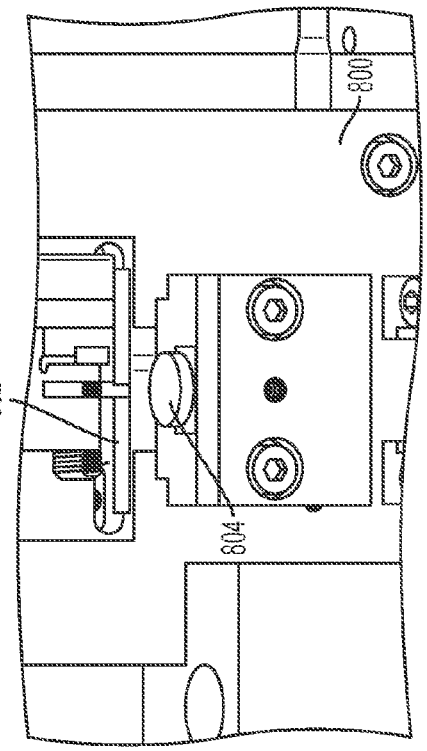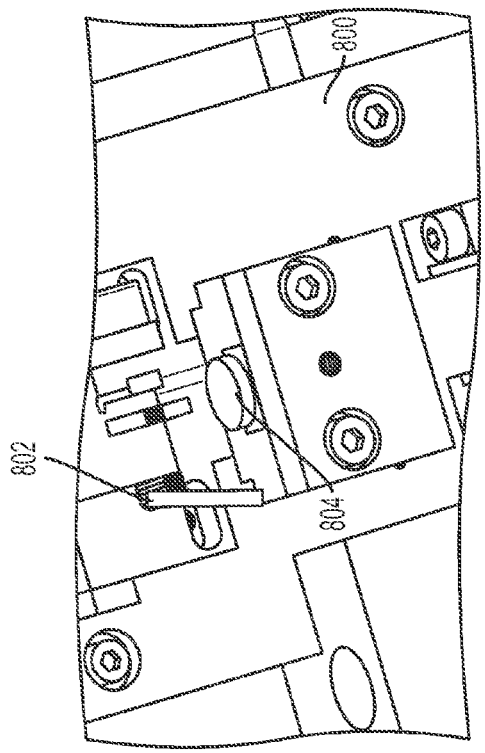
FIG. 8B
FIG. 8A
FIG. 8C

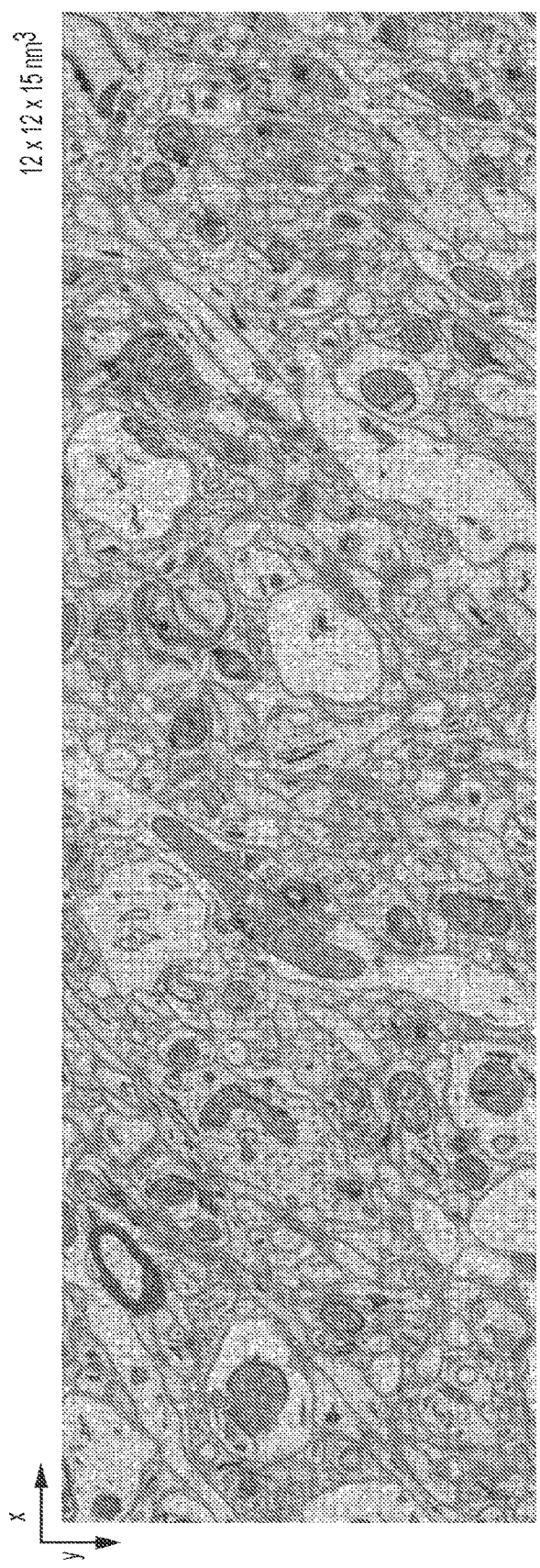
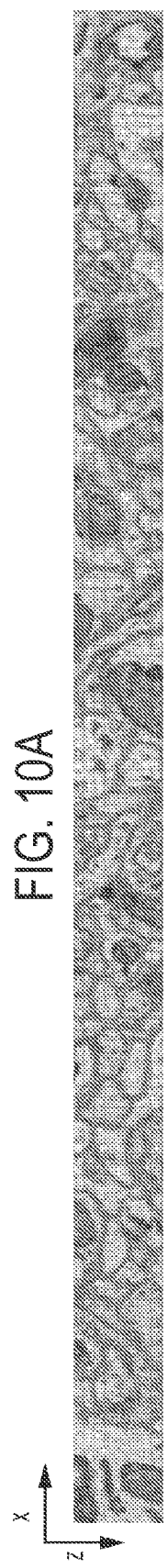
FIG. 10A
FIG. 10B

MINIATURE SERIAL SECTIONING MICROTOME FOR BLOCK-FACE IMAGING

CROSS-REFERENCE TO RELATED APPLICATIONS

This application is the U.S. National Stage of International Application No. PCT/US2015/030359, filed on May 12, 2015, which claims the benefit of U.S. Provisional Application No. 61/991,929, filed on May 12, 2014, which is incorporated by reference herein.

FIELD

The present disclosure relates to microtome devices and methods of their use, and in particular to microtome devices designed for use in block-face imaging applications, including optical or electron-based imaging.

BACKGROUND

One application of block-face imaging technologies is serial block-face scanning electron microscopy (sometimes referred to as SBEM, SBSEM, and/or SBFSEM), which refers to a process of generating multiple two-dimensional images of a sample at sequential planes along a third dimension, thereby producing data about the three-dimensional structure of the sample. The SBSEM technique can be used to study many different types of biological specimens, and is often used to study brain tissues. It is of particular use to collect high resolution anatomical data, for example when mapping axons in the brain and neuronal circuit connectivity. One SBSEM process includes the use of a scanning electron microscope (SEM) to obtain the two-dimensional images by collecting secondary and backscattered electrons, and a microtome (sometimes referred to as an "ultra-microtome") to remove very thin (e.g., in the tens of nanometers range) portions of the top of the sample between successive images. By mounting a microtome in the vacuum chamber of the scanning electron microscope, the process can be made more efficient. Prior microtomes have various drawbacks, as described further herein. Accordingly, there exists a need for improvements in microtome technologies.

SUMMARY

In some embodiments, a microtome for removing a thin portion of the top of a sample comprises a base plate, a pedestal coupled to the base plate such that the pedestal can be moved from an imaging location to a cutting location, wherein the pedestal has an exposed surface on which the sample can be mounted, a blade coupled to the base plate such that a blade location with respect to the base plate can be adjusted by moving the blade in a direction perpendicular to the exposed surface of the pedestal when the pedestal is in the imaging location, to selectively vary a distance between the blade and the base plate, wherein the cutting location is closer to the blade than the imaging location.

In some examples, the microtome is mounted on a fluorescence microscope configured to image a surface of the sample using a camera. In some examples, the microtome is mounted on a cathodoluminescence microscope configured to image a surface of the sample using a camera. In some examples, the microtome is mounted on a photoemission electron microscope configured to image a surface of the sample using a camera. In some examples, the blade is mounted on a first computer-controlled linear actuator coupled to the base plate. In some examples, the pedestal is mounted on a lever coupled to the base plate by a pivot bearing. In some examples, the pedestal can be rotated about the pivot bearing by actuation of a second computer-controlled linear actuator coupled to the base plate.

In some examples, the first actuator is configured to receive a control signal to direct movement of the blade, the microtome further comprising a sensor coupled to the first actuator and configured to produce an output signal indicating the blade location with respect to the base plate, and a computer program configured to receive the output signal from the sensor, generate the control signal based at least in part on the output signal from the sensor, and transmit the control signal to the first actuator.

In some examples the microtome further comprises a sample positioned on the pedestal. In some examples, a working distance between the sample and a pole piece of the scanning electron microscope can be selected from a range of available working distances. In some examples, a voltage is applied to the sample. In some examples, the sample is electrically isolated from the microtome. In some examples, the blade is a piezo-electrically controlled oscillating diamond blade. In some examples, the microtome further comprises a computing apparatus including a processor and memory, the memory storing computer readable instructions for combining a plurality of images of the sample to create a three-dimensional representation of the sample.

In some embodiments, a microtome configured to be installed within a scanning electron microscope comprises a blade coupled to an actuator, wherein the actuator is coupled to a stage of the scanning electron microscope such that the actuator can move the blade with respect to the stage in a direction parallel to a beam axis of the scanning electron microscope, and wherein the actuator is configured to receive a control signal to direct movement of the blade, a sensor coupled to the actuator and configured to produce an output signal indicating the blade location with respect to the base plate, and a computer program configured to receive the output signal from the sensor, generate a control signal based at least in part on the output signal from the sensor, and transmit the control signal to the actuator.

In some examples, a microtome further comprises a pedestal coupled to the stage such that the pedestal can be moved from an imaging location on the beam axis to a cutting location off the beam axis, wherein the cutting location is closer to the blade than the imaging location.

In some embodiments, a method comprises positioning a sample at an imaging location on a microtome within a scanning electron microscope, wherein the imaging location is on a beam axis of the scanning electron microscope, imaging a first exposed surface of the sample, setting a height of a blade of the microtome, moving the sample from the imaging location to a cutting location, wherein the cutting location is closer to the blade than the imaging location and not on the beam axis, moving the sample across the blade to remove a portion of the sample and reveal a second exposed surface of the sample, moving the sample to the imaging location, and imaging the second exposed surface of the sample.

In some examples, a method further comprises, after setting the height of the blade, maintaining the height of the blade under feedback control. In some examples, a method further comprises, prior to imaging the second exposed surface, focusing an electron beam of the scanning electron microscope at the second exposed surface. In some examples a method further comprises, prior to imaging the second exposed surface, adjusting the sample along the beam axis. In some examples, a method further comprises, after adjusting the sample along the beam axis, focusing an electron beam of the scanning electron microscope at the second exposed surface.

In some examples, the act of imaging the first exposed surface of the sample comprises using the scanning electron microscope to capture a plurality of constituent images of the first exposed surface, and stitching the plurality of constituent images together to form a composite image of the first exposed surface. In some examples, a method further comprises tilting the microtome such that the beam axis is not perpendicular to the exposed surface of the sample. In some examples, a method further comprises rotating the microtome. In some examples, a method further comprises cleaning the blade with a Styrofoam cleaning rod. In some examples, the microtome is mounted on an intermediate stage and the intermediate stage is mounted on a built-in stage of the scanning electron microscope.

The foregoing and other features and advantages of the disclosed technology will become more apparent from the following detailed description of several embodiments, which proceeds with reference to the accompanying figures.

BRIEF DESCRIPTION OF THE DRAWINGS

FIGS. 2A-2C show portions of the microtome of FIG. 1 at a larger scale.

FIG. 7 is a side view of a microtome in which a voltage has been applied to an electrically isolated sample.

FIGS. 8A-8C illustrate the ability to control the tilt of a sample using a microtome such as the microtome of FIG. 1 in a scanning electron microscope.

FIGS. 10A and 10B illustrate XY and XZ views, respectively, of a 15 nanometer thin section of tissue cut using a disclosed microtome.

DETAILED DESCRIPTION

Figure 1:
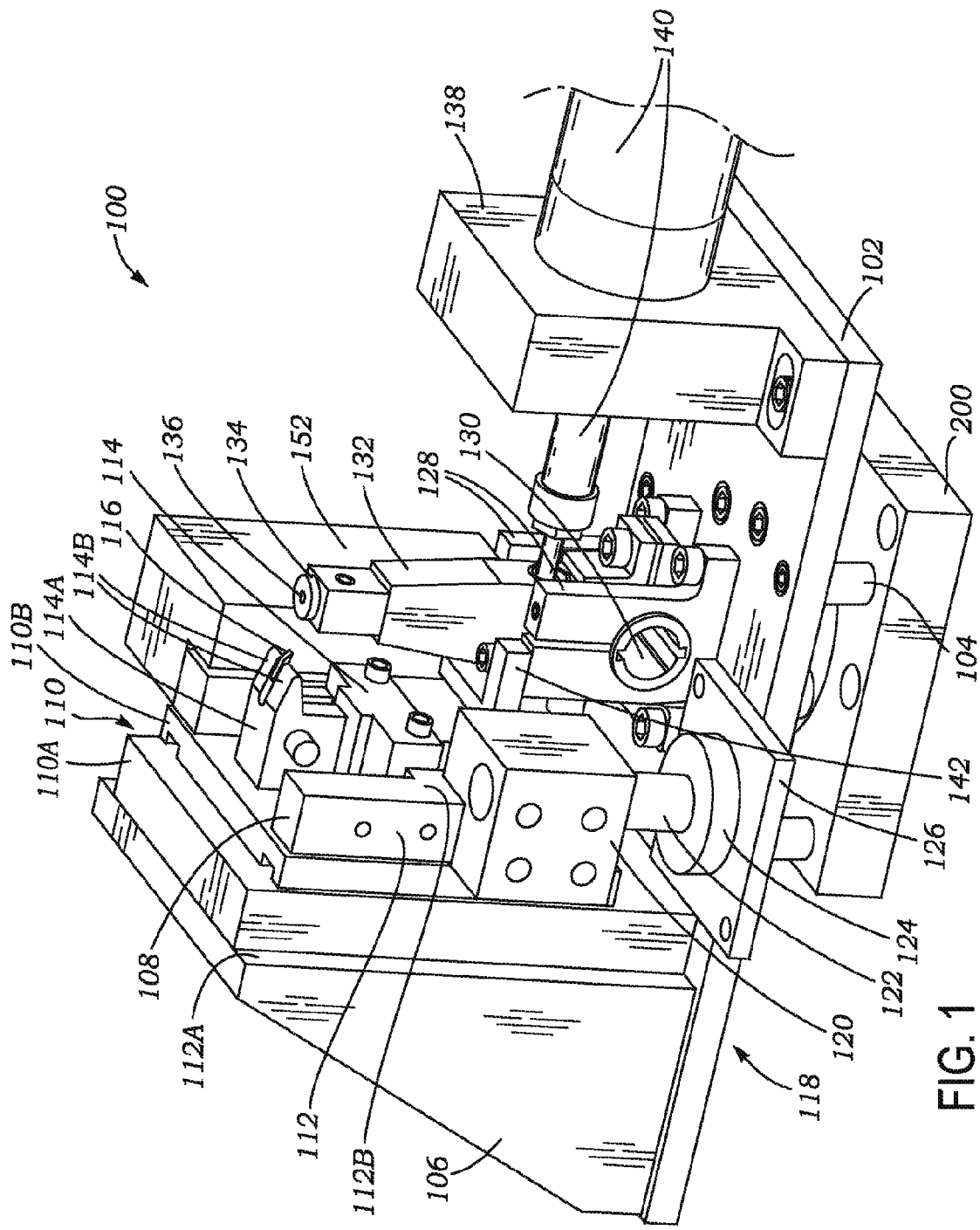
FIG. 1 is a top perspective view of an exemplary microtome.

The microtomes described herein can be used in a variety of techniques for microscopic analysis, such as in scanning electron microscopy, light-based (optical, e.g., fluorescence) microscopy, cathodoluminescence microscopy, or with combinations of these techniques. For example, a sample can be mounted on a microtome as described below, which can be directly mounted under the objective of an ordinary light-based (optical) (e.g., fluorescence) microscope. Such embodiments can operate in atmospheric conditions and in the absence of a scanning electron microscope. Such techniques can take advantage of the various fluorescence microscopy techniques known in the art (e.g., multi-photon microscopy, super-resolution microscopy, etc.).

In some examples, the microtomes described herein can be used in both optical and/or cathodoluminescence microscopy and scanning electron microscopy and images of successive exposed surfaces can be captured and stored. The images can also be digitally analyzed and recombined to provide three-dimensional images or representations of the tissue at a high degree of microscopic resolution, for example, to determine or map neuronal circuitry of a subject. This can be accomplished in some embodiments by imaging a sample through a view port in the internal vacuum chamber of a scanning electron microscope using, for example, a fluorescence detector, a camera, or a CMOS sensor. In some cases, a fluoroscopic and/or cathodoluminescence image can be taken for every exposed surface of the sample during an SBEM process, such that every scanning electron microscope image has a corresponding fluoroscope and/or cathodoluminescence image. Portions of the following description proceed with reference to use of a microtome in SBEM processes, but the present disclosure is generally applicable to the use of microtomes in any application.

The microtomes described herein can be used to study any of various types of sample materials and for various purposes, including the examination of tissue specimens for the study of cellular biology, cancer biology, and/or immunology. The microtomes are particularly well-suited for use with plastic-embedded biological tissue samples such as plastic-embedded brain tissues.

Scanning electron microscopy allows very high-resolution imaging of samples, which has led to its use in a wide variety of fields. Many commercial scanning electron microscopes contain an internal, accessible, vacuum chamber in which a sample is positioned for imaging by the microscope. The internal chamber is accessed through a door in the side of the microscope, which is closed to provide the chamber with an airtight seal. The internal chamber is then evacuated of air to reduce interference with the imaging process (e.g., through scattering of the electron beam by gas molecules).

Many scanning electron microscopes also contain a stage on which the sample to be imaged is positioned, and the stage is translated linearly along or with respect to three axes, for example, a z-axis aligned with the electron beam of the microscope and x- and y-axes perpendicular to the z-axis. The stage can also be rotated about the z-axis and tilted about at least one of the x- and y-axes such that the face of the stage can be rotated and tilted with respect to the electron beam. In some electron microscopes, the stage can be rotated 360° about the z-axis and tilted over a range of 90° about one of the x- and y-axes. Rotating the microtome about the z-axis can be used to align a sample under the electron beam.

In the study of materials, and in particular of biological tissues, data describing the three-dimensional structure of a sample can be highly desirable. To obtain three dimensional data, microtomes have been developed that can be installed within the vacuum chamber of a scanning electron microscope. A sample is mounted on the microtome and positioned to be imaged by the microscope. Once the exposed surface of the sample has been imaged, the microtome is used to remove a very thin portion of the top of the sample, exposing a new surface to be imaged. This process can be repeated until a desired number of images have been taken, or until a desired thickness of the sample has been imaged. The series of images thus taken can illustrate the three dimensional structure of the sample.

Known microtome devices suffer from various drawbacks. As one example, known microtomes move a blade across the sample to remove a thin portion of the top of the sample. Because the sample is positioned directly underneath the detector and the pole piece of the microscope, debris from the slicing of the sample can contact or become stuck to the detector and/or the pole piece of the electron column, interfering with the operation of the microscope. In some cases, a pressure differential exists at the entrance of the pole piece of an electron microscope, increasing the chances of debris entering the electron column and exacerbating this problem. Further, in order to allow space for the blade to move across the top of the sample, sufficient space must be provided between the sample and the detector, thereby reducing the range of possible working distances. In particular, this limits the extent to which the working distance can be reduced, which in turn can limit the quality of the data which can be obtained. For example, reducing the working distance between the sample and the detector can improve the signal to noise ratio in the resulting data.

As another example, a known microtome available from Gatan Inc. of Warrendale, Pa., is mounted on a custom steel door. To install this microtome in a scanning electron microscope, the original stage and door of the microscope must be removed, and the custom steel door is fitted in the original's place. This makes the microtome relatively heavy and difficult to install. Further, this microtome only allows translation of the sample along the x-, y-, and z-axes, but does not allow the sample to be tilted or rotated, as the built-in stage allows. Further still, the translation this device provides along the x- and y-axes is not truly rectilinear. Rather, it is understood that the Gatan microtome provides translation along large parabolic arcs such that the translation approaches, but is not quite, rectilinear. Known microtomes have other drawbacks, which are described in greater detail below.

The microtome devices described herein allow a sample to be cut at a location removed from the electron beam axis, thus reducing the chances of interference from debris, and allowing imaging at a greater range of working distances. This can be advantageous by permitting the working distance to be reduced further than in known devices and providing a greater range of working distances to choose from. The microtome devices described herein can also be relatively lightweight and thus easier to install, and in some embodiments are designed to be installed on the built-in stage of various scanning electron microscopes such that a sample's position and orientation can be finely controlled along three axes of true rectilinear translation (over a range of many centimeters) and about two axes of rotation. The microtomes described herein are capable of reproducibly cutting very thin sections from the top of a sample. The microtomes described herein have additional advantages, which are described in greater detail below.

FIGS. 1 and 2A-2C show an exemplary microtome 100 suitable for use in a scanning electron microscope. The microtome 100 is mounted on the stage of the scanning electron microscope when used therein, to control the translation and rotation of the microtome 100. The microtome 100 can be mounted flush with the stage of the microscope, or can be coupled to and spaced apart from the stage by a plurality of posts. The microtome 100 can be used in connection with any of various commercially available scanning electron microscopes having an internal chamber large enough to fit the microtome therein (exemplary overall dimensions of the microtome 100 are provided below). For example, the microtome 100 can be used in the NOVA NANOSEM 50 series scanning electron microscopes commercially available from FEI company of Hillsboro, Oreg. One suitable scanning electron microscope is the FEI NanoSEM 450 device.

The microtome 100 includes a base plate 102 coupled to the stage. A bracket 106 is coupled to the base plate 102 and includes a vertical surface 108 to which a linear actuator 110 is mounted. Any of various suitable linear actuators can be used. As examples, the N-661 Miniature Linear Stage with NEXACT Drive, previously commercially available from Physik Instrumente, and its replacement product Linear Piezo Stage LPS-45, currently commercially available from Physik Instrumente, in combination with their associated controller units, are suitable linear actuators. The linear actuator 110 can generate translation of its platform 110B with respect to its main body 110A.

An H-shaped mounting element 112 having two vertical posts 112A and a central crossbar 112B is mounted to the exposed surface of the platform 110B. A blade support 114 including a vertical portion 114A and two horizontally protruding arms 114B is mounted to the central crossbar 112B. The arms 114B are spaced apart from one another and extend away from the vertical portion 114A parallel to one another such that a blade 116 can be mounted between their terminal ends. Suitable blades are known in the art. Blades particularly well suited for use in microtome 100 include piezo-electrically controlled oscillating diamond blades, such as those described in Studer, et al., *Minimal Compression of Ultrathin Sections with use of an Oscillating Diamond Knife*, Journal of Microscopy, Vol. 197, Pt. 1, pages 94-100 (January 2000). A variety of particularly well-suited, commercially available blades are offered by DiATOME U.S.

Figure 2C:
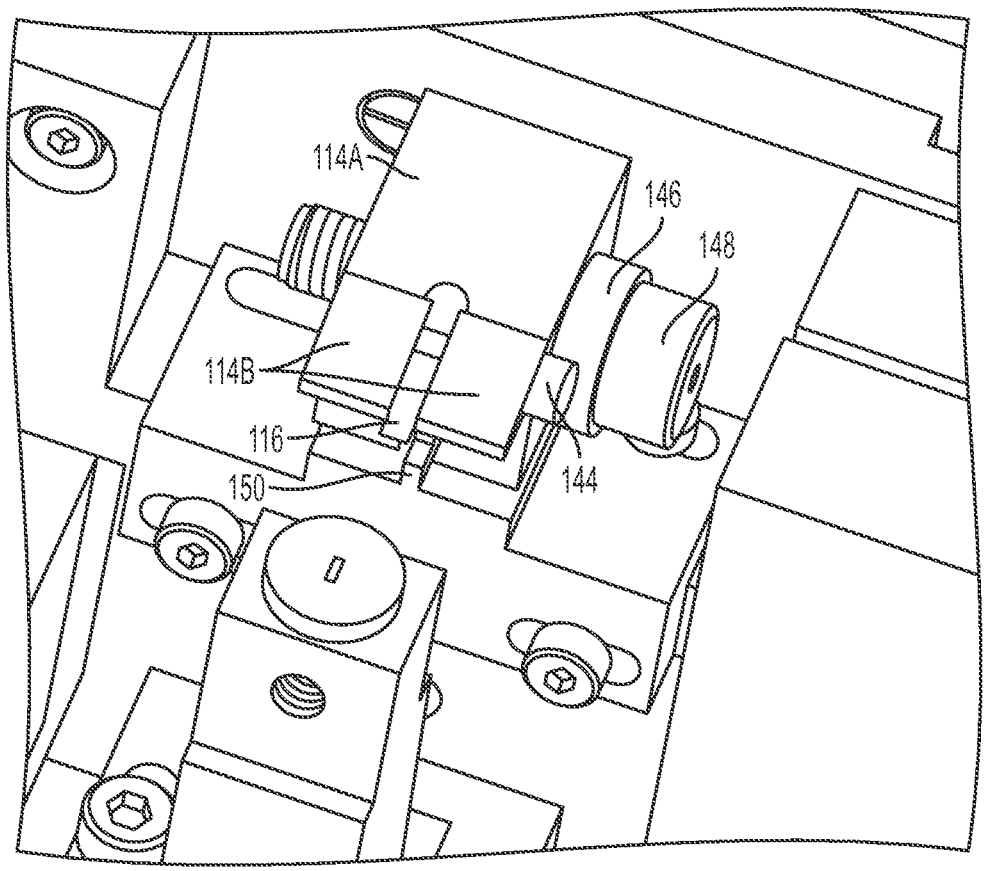

As shown in greater detail in FIGS. 2B and 2C, the blade 116 is mounted between the terminal ends of the arms 114B, and a screw 144 is threaded through the arms 114B and tightened so that the blade 116 is pinched between the arms 114B. A piezo actuator 146 is coupled to the vertical portion 114A of the blade support 114 by a screw 148 secured to the blade support 114 by a nut on the end of the screw 148 opposite the piezo actuator 146. The blade support 114 can be coupled to a flexure element 150 which couples the blade support 114 to the rest of the microtome 100. The flexure element can be a narrow, pliable, metallic element having sufficient flexibility such that actuation of the piezo actuator 146 causes the blade support 114 to oscillate back and forth as the flexure element 150 flexes. The flexure element 150 can have a width of 1 mm. The piezo actuator 146 can be configured to oscillate at a resonant frequency of the blade support 114 on the flexure element 150. One suitable piezo actuator is the high vacuum compatible PD080.31 through hole piezo actuator, available from PI Ceramic, and associated signal amplification and conditioning equipment available from Physik Instrumente.

The microtome 100 also includes a sensor assembly 118 (FIG. 1), which includes a sensor clamp 120 for holding the sensor in place, a capacitive sensor including a shaft 122 and a capacitive sensor module 124, and a target plate 126 coupled to the base plate 102. Various suitable capacitive sensors are commercially available, with one example being the D-510 PISECA Capacitive Sensors and associated signal conditioning equipment available from Physik Instrumente, which are capable of measurement with nanometer resolution. The capacitive sensor can provide an output signal indicating a distance between the exposed bottom surface of the capacitive sensor module 124 and the exposed upper surface of the target plate 126. The sensor assembly 118 is coupled to a vertical post 112A of the mounting element 112 and thus, given knowledge of the dimensions of the various components of the microtome 100, the output signal can indicate the height of the blade 116 with respect to a sample 136.

The output signal from the capacitive sensor can be run through a data conditioning and/or acquisition system such as the 18-Bit, 625 kS/s, NI USB-6289 M Series Multifunction DAQ system, commercially available from National Instruments Corporation, and into a software program such as a program implemented in MATLAB, commercially available from Mathworks, Inc. The program can be configured to receive the output signal from the capacitive sensor, to receive input from a user (e.g., a desired height of the blade 116), and to provide an output signal to the actuator 110 to control movement of the platform 110B. Upon receiving input indicating that the blade 116 is to be moved to a desired height, the program can compute a specified height of the platform 110B which will position the blade 116 at the desired height. The program can then send a signal to the actuator 110 including a command to move to the specified height. The program can further monitor the signal from the capacitive sensor to determine whether the blade is actually moved to and kept at the specified height.

If the signal from the capacitive sensor indicates that the actual blade height is lower than the desired blade height, then the program can send a new signal to the actuator 110 including a command to move to a new height which is greater than the specified height. If the signal from the capacitive sensor indicates that the actual blade height is higher than the desired blade height, then the program can send a new signal to the actuator 110 including a command to move to a new height which is less than the specified height. This process can run continually, creating a closed control loop (or feedback loop) (e.g., using a PID control loop feedback mechanism) that maintains the blade 116 at the desired height based on the signal from the capacitive sensor. This can help improve the precision of the microtome system, including the precision and uniformity with which it removes material from the top of the sample 136.

The microtome also includes two pivot support elements 128 spaced apart from one another and coupled to the base plate 102, a pivot bearing 130 mounted to and spanning between the pivot support elements 128, and a rotatable lever 132 mounted on the pivot bearing 130 for rotation about the axis of the pivot bearing. The pivot bearing 130 includes a stationary portion rigidly coupled to and supported by the pivot support elements 128, and a rotatable portion freely rotatable with respect to the stationary portion rigidly coupled to and supporting the lever 132. Various suitable commercially available pivot bearings can be used, such as the 6016-800 pivot bearing commercially available from the Riverhawk company. At the top of the rotatable lever 132, the microtome 100 includes a pedestal 134 on which the sample 136 to be studied can be mounted. Suitable pedestals include specimen mounts for scanning electron microscopes, such as the EMS Aluminum Specimen Stub 75638-10, commercially available from Electron Microscopy Sciences.

The microtome 100 also includes a clamp 138 coupled to the base plate 102 and a linear actuator 140 clamped within the clamp 138. Any of various commercially available linear actuators can be used, with one particularly well-suited actuator being the N-381 NEXACT Linear Actuator, Manipulator, Piezo Stepper product and associated controller available from Physik Instrumente. The linear actuator 140 is coupled to the rotatable lever 132 such that the actuator 140 can control the rotation of the lever 132 about the pivot bearing 130. More specifically, the actuator 140 terminates at a ball bearing, which is in engagement with a sapphire pad located inside the lever 132. A sapphire pad can provide a very flat and durable surface for engaging the actuator 140. Suitable sapphire pads include those sold under the model number P25SK2-Polaris-K1 by Thorlabs, Inc.

In some cases, the lever 132 can be biased (e.g., the lever 132 can be weighted) to rotate about the pivot bearing 130 away from the blade 116. The actuator 140 can push against the sapphire pad to actuate the lever 132 to move the sample 136 toward the blade 116. In one specific embodiment, the lever 132 can be weighted such that it is biased to come to rest at about 1 degree of rotation about the pivot bearing 130 farther from the blade 116 than an electron beam of a scanning electron microscope. The actuator 140 can engage the sapphire pad to rotate the lever 132 by 1 degree toward the blade 116 such that the sample 136 is positioned in the electron beam of the scanning electron microscope. The actuator 140 can engage the sapphire pad to rotate the lever 132 by about 10 degrees such that the sample 136 is positioned within the region of the blade 116.

To prevent the actuator 140 rotating the sample 136 too far in the direction of the blade 116 and the actuator 110, the microtome also includes a pivot stopper 142 coupled to the pivot support elements 128 and extending between the lever 132 and the actuator 110. The microtome 100 can also include a weight 152, such as a block of steel, to add additional weight to the actuator 110 to stabilize the blade 116 and maintain the location of the blade 116 as the sample 136 is translated across the blade 116.

The actuator 140 can be used to move the sample 136 across the blade 116, e.g., to remove a portion of the exposed surface of the sample 136. For example, the MATLAB program described above can be configured to receive input from a user regarding the desired motion of the sample 136, and to provide an output signal to the actuator 140 to control movement of the lever 132 and thus the sample 136. Upon receiving input indicating that the sample 136 is to be moved to a desired location, the program can compute a specified location of the actuator 140 which will position the sample at the desired location. The program can then send a signal to the actuator 140 including a command to move to the specified location.

In some cases, a sample to be studied can be embedded in plastic (e.g., in an epoxy resin) to facilitate the precise cutting and imaging of the sample. Methods of preparing samples for use in a microtome for serial block-face scanning electron microscopy are known in the art. As one example of such a method, a sample of tissue to be studied can be cut to size and then embedded in a liquid epoxy resin in a mold, and the epoxy resin can then be cured in an oven. The sample and epoxy in which it is embedded can be cut out of the mold and glued to the mount or pedestal on which it will be supported on the microtome. For example, the sample can be glued to the pedestal using the same epoxy in which the sample was embedded.

Once the sample has been glued to the pedestal, unneeded portions of the sample can be removed using a commercial ultra-microtome, thereby resulting in a truncated-pyramidshaped or trapezoidal-prism-shaped sample with tissue exposed at its sides. Such shapes provide relatively rigid and stable samples which can be more accurately and consistently cut than samples of other shapes. The sample can then be coated in a conductive material such as gold, so as to ground the sides of the sample to the pedestal, allowing dissipation of electrons from the sample and preventing accumulation of electrostatic charge during imaging. The coating can then be removed from the top of the sample to expose the upper surface of the sample for imaging in a scanning electron microscope.

FIG. 2A shows an enlarged view of portions of the microtome 100, wherein the sample 136 is situated under the pole piece and on the beam axis of the scanning electron microscope. FIG. 2B shows an enlarged view of the portions of the microtome of FIG. 2A, after the MATLAB program has sent a command to the actuator 140 and the actuator 140 has responded to the command by actuating the lever 132 to move the sample 136 toward the blade 116 and out from under the pole piece and away from the beam axis of the scanning electron microscope.

The microtomes described herein are capable of reproducibly cutting very thin sections from the top of a sample. The microtomes can cut sections having a thickness equal to the resolution of the capacitive sensor, which can be less than 10 nanometers. In cases where a microtome is used in a scanning electron microscope, section thickness is limited by the electron dose imparted to the sample and the sample's plastic embedding material, which, as described above, can change the material properties of the plastic embedding material (e.g., by breaking bonds in the plastic polymer) thus making slicing the sample more difficult and leading to chatter and/or less consistent section thicknesses. It has been found that 30 nanometers is a suitable section thickness for reducing this effect. Thus, in SBEM applications, the microtomes described herein are sufficiently precise that they are not the factor limiting reduction of the section thickness. In cases where a microtome is used in an optical microscope, section thicknesses as small as the resolution of the capacitive sensor can be used.

The components of the microtome described above can be fabricated from any of various suitable materials including aluminum, titanium, and/or stainless steel. The microtome can include a thermocouple to monitor the temperature of the components, to mitigate thermal effects as needed. It has been found that the microtome described above can have a weight of less than 1 kg, an overall width of 235 mm, depth of 73 mm, and height of 75 mm, and can be built for significantly less expense than known commercially available microtomes. Slight rearrangements of the elements of the microtome can be made to adjust the dimensions of the microtome, for example, to accommodate specific SEM vacuum chambers. Based on its weight, this microtome can be easier to install in a scanning electron microscope than other known microtomes. Based on its overall dimensions, the microtome can fit easily within a 30 cm vacuum chamber of a scanning electron microscope. It is also compatible with optical microscopes, and can be fabricated from non-magnetic materials (e.g., aluminum, platinum) so as to prevent or reduce interference with the magnetic field of an SEM in an immersion lens operating mode.

Figure 2D:
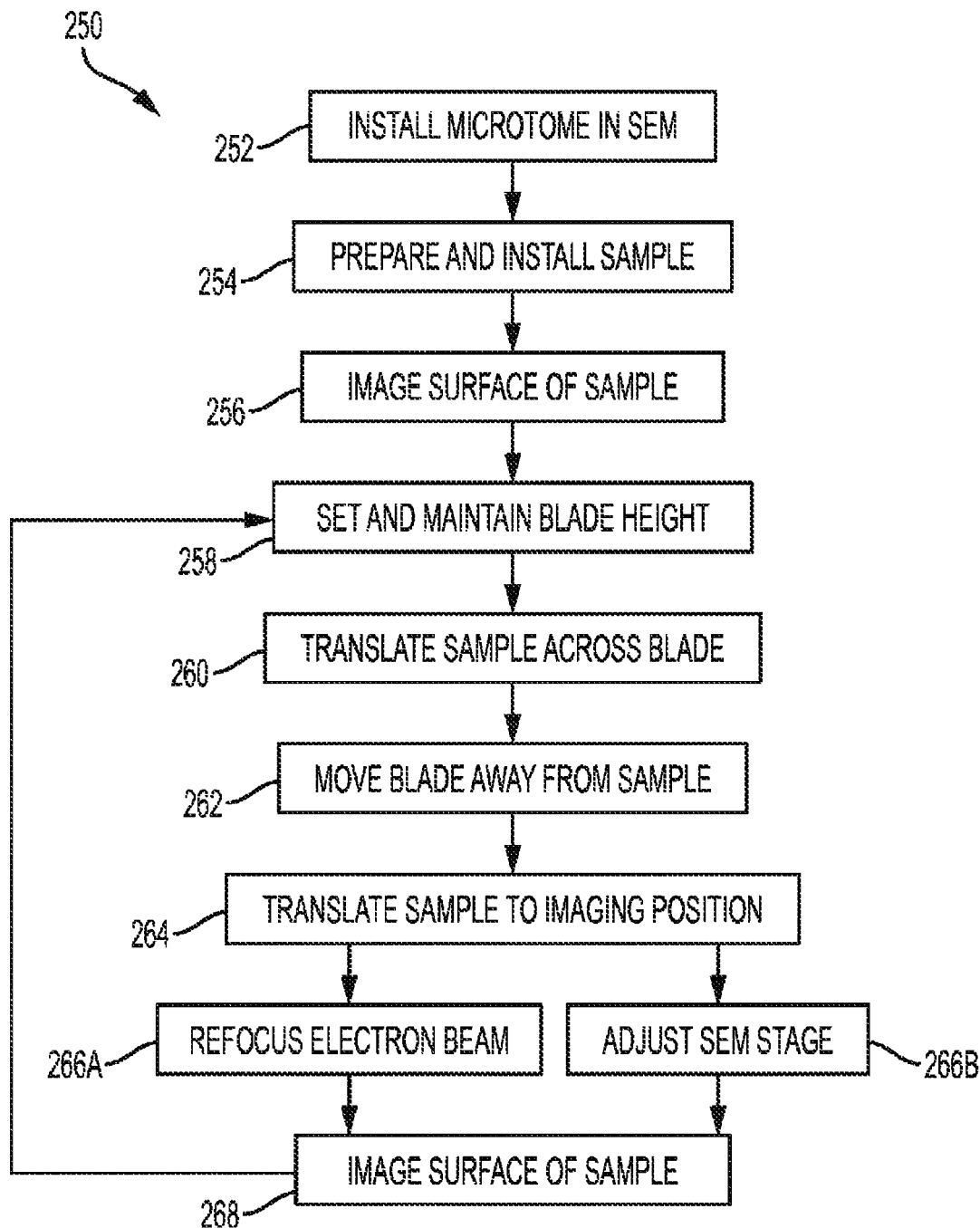
FIG. 2D illustrates a method of using the microtome of FIG. 1.

FIG. 2D illustrates an exemplary method 250 of using the microtome 100. At 252, the microtome 100 can be installed in the vacuum chamber of a scanning electron microscope. At 254, a sample can be prepared for study and installed on the microtome 100. At 256, the exposed surface of the sample can be imaged using the scanning electron microscope. At 258, the blade height can be set and maintained under feedback control, and the piezo actuator 146 can be actuated to cause oscillation of the blade. At 260, the sample can be translated across the blade to remove a thin portion of the sample, and the actuation of the piezo actuator 146 can be discontinued to suspend the oscillation of the blade. At 262, the knife blade can be retracted upwards away from the sample. At 264, the sample can be translated back to its original imaging position under the electron column of the scanning electron microscope.

Once the sample has been returned to the imaging position, the exposed surface of the sample is at a slightly lower location than it was for the imaging of step 256, due to the removal of the top portion of the sample by the blade. Thus, after the sample is returned to the imaging position at 264, the system can be adjusted to compensate for this change. This adjustment can be accomplished at 266A by refocusing the electron beam of the scanning electron microscope at the new exposed surface. Alternatively (or in addition), this adjustment can be accomplished at 266B by translating the built-in stage of the scanning electron microscope to move the sample upward so that the exposed surface of the sample is at the same location as it was for the imaging of step 256. At 268, the exposed surface of the sample can be imaged using the scanning electron microscope, and the process can repeat until sufficient data has been collected.

In some cases, as a sample is translated across a blade, debris can build up on the blade, reducing its precision and consistency, and/or remain on the exposed surface of the sample, potentially introducing errors into images taken of the surface. In order to prevent the build-up of debris on the blade 116, a piece of STYROFOAM or other suitable material can be mounted to the pedestal 134 behind the sample 136, that is, so that the sample 136 is between the material and the blade 116 when the sample is in the imaging position. Thus, the lever 132 can be moved toward the actuator 110 so that the sample 136 is cut, and the lever 132 can be moved further so that the material contacts the blade 116 to remove any debris remaining thereon.

If a scanning electron microscope image of the exposed surface reveals that debris is present on the surface, then steps can be taken to remove the debris from the surface so a more complete image can then be obtained. In order to remove debris remaining on the exposed surface of the sample 136, the sample 136 can for example be moved across the blade 116 a second time, so that the blade 116 can sweep any debris off the face of the sample 136. This can be done by maintaining the blade 116 at the same height as for the initial cut, or by first moving the blade 116 a small distance away from the exposed surface of the sample 136 so that no additional portion of the sample 136 is inadvertently removed.

Figure 3A:
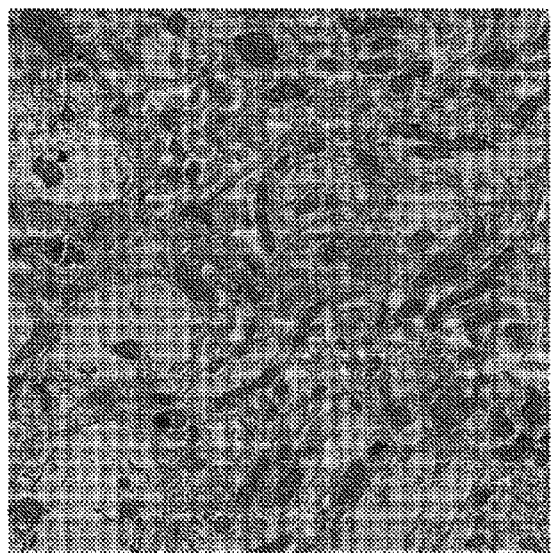
FIGS. 3A-3O are several successive scanning electron microscope images of a tissue sample generated during serial block-face scanning electron microscopy, together with images illustrating the computed difference between the successive scanning electron microscope images of the tissue sample.
Figure 3B:
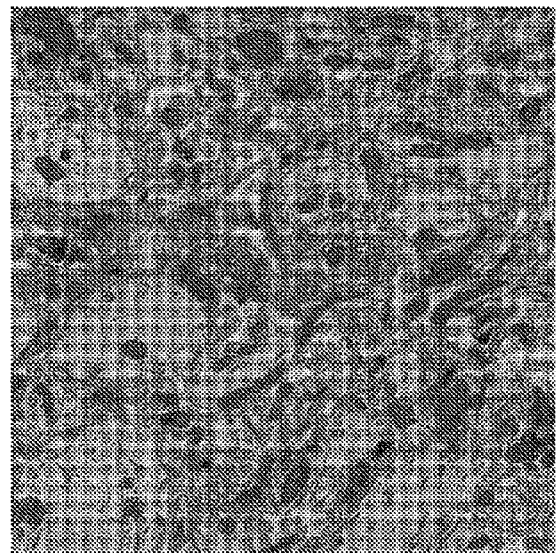
Figure 3C:
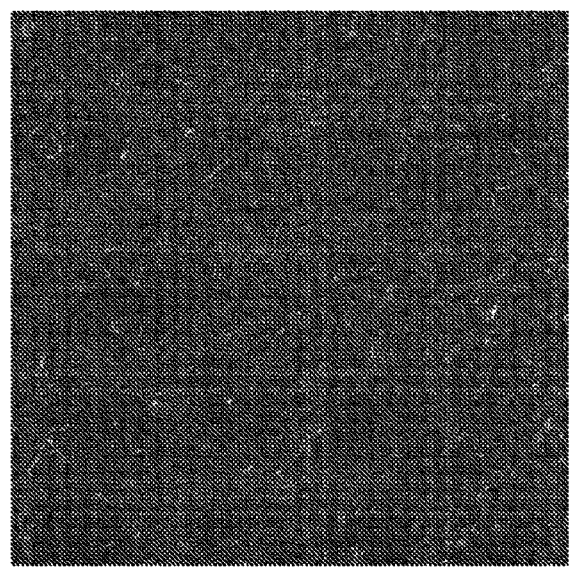

FIGS. 3A and 3B are scanning electron microscope images of sequential exposed surfaces of a tissue sample generated during serial block-face scanning electron microscopy using a microtome as described above to remove a slice of thickness 40 nanometers from the top of the sample. Thinner slices can also be removed with certain embodiments, such as down to 15 nanometer thin sections as is shown in FIGS. 10A and 10B. FIG. 3C is an image illustrating the computed difference between the sequential images of FIGS. 3A and 3B. In FIG. 3C, darker regions indicate less difference between the sequential images and lighter regions indicate greater difference between the successive images. As shown in FIG. 3C, the successive images are largely similar, indicating that the structure of the tissue sample changes only slightly across the thickness of the slice removed from the top of the sample by the microtome, reflecting the ability of the microtome to remove a very small portion of the sample. As also shown in FIG. 3C, the differences between the successive images are relatively consistent throughout the full extent of the images, indicating that the thickness of the portion removed from the sample was similarly consistent across the surface of the sample. These results illustrate the ability of the microtomes described herein to remove very thin portions of a sample with great consistency, e.g., without the knife blade skipping across the surface of the sample (sometimes referred to as "chatter").

Figure 3D:
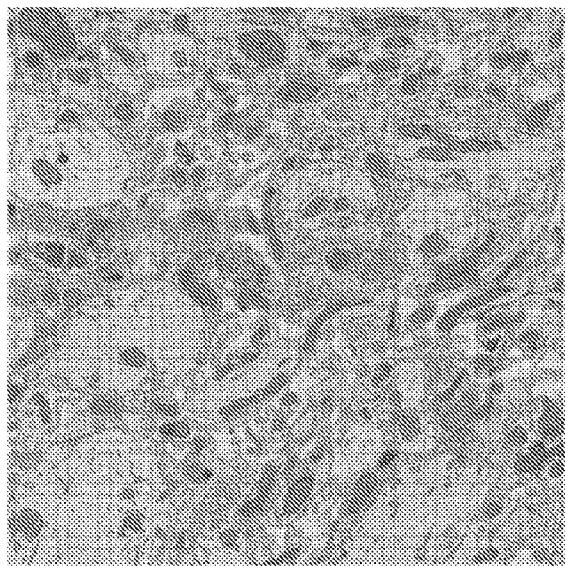
Figure 3E:
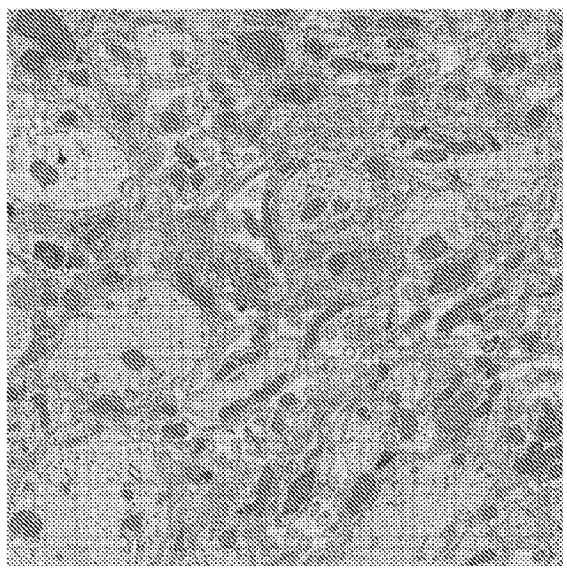
Figure 3F:
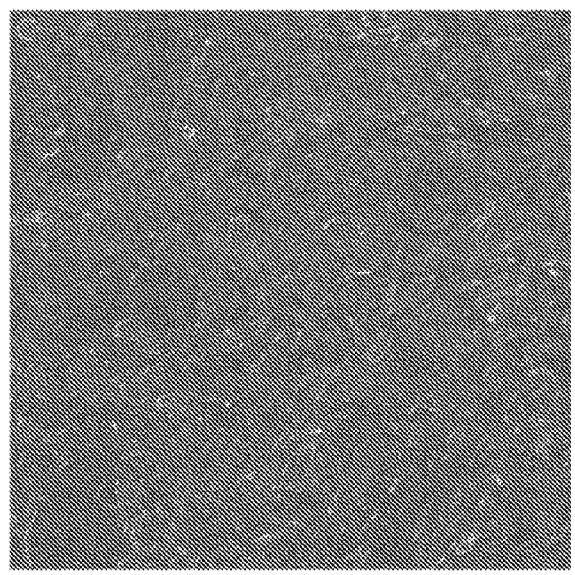
Figure 3G:
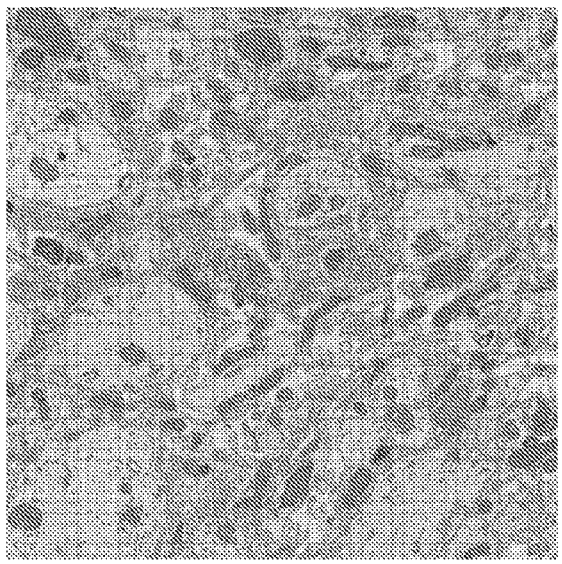
Figure 3H:
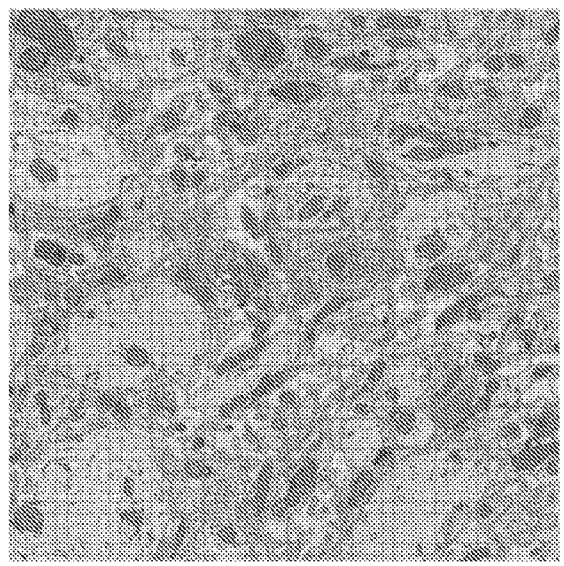
Figure 3I:
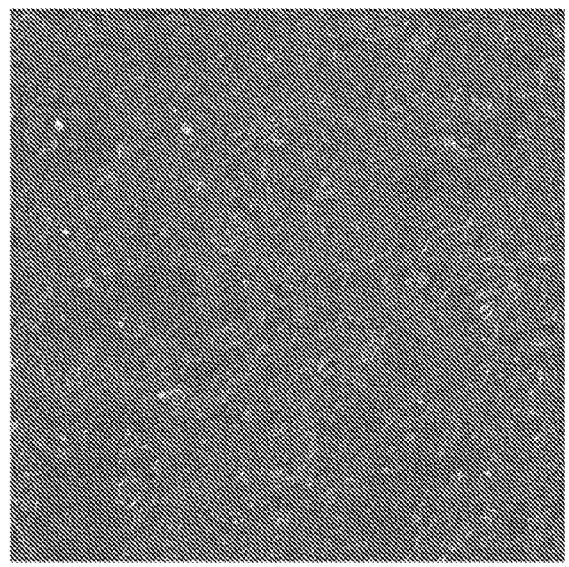
Figure 3J:
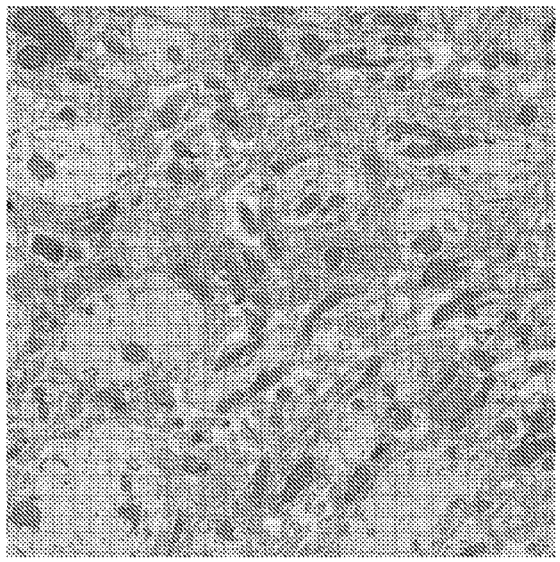
Figure 3K:
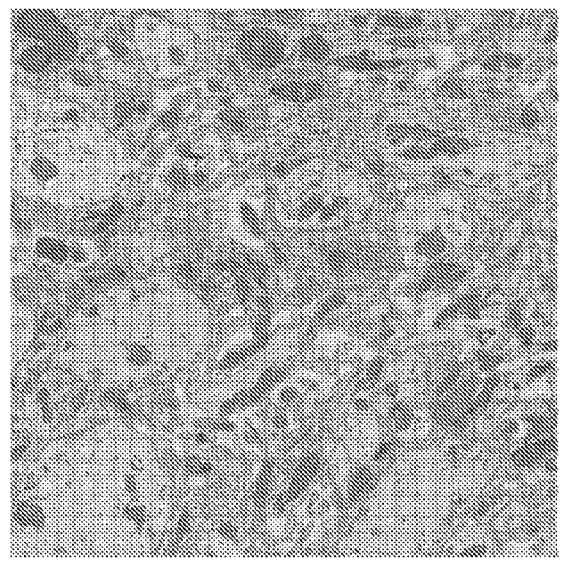
Figure 3L:
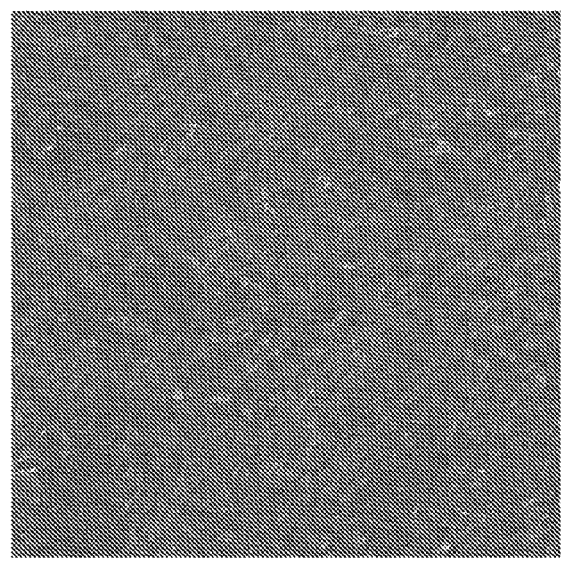

FIG. 3D is the same photomicrographic image as FIG. 3B. FIGS. 3D and 3E are scanning electron microscope images of sequential exposed surfaces of a sample generated as described above. FIG. 3F is an image illustrating the computed difference between the sequential images of FIGS. 3D and 3E. FIG. 3G is the same photomicrographic image as FIG. 3E. FIGS. 3G and 3H are scanning electron microscope images of sequential exposed surfaces of a sample generated as described above. FIG. 3I is an image illustrating the computed difference between the sequential images of FIGS. 3G and 3H. FIG. 3J is the same photomicrographic image as FIG. 3H. FIGS. 3J and 3K are scanning electron microscope images of sequential exposed surfaces of a sample generated as described above. FIG. 3L is an image illustrating the computed difference between the sequential images of FIGS. 3J and 3K. FIG. 3M is the same photomicrographic image as FIG. 3K. FIGS. 3M and 3N are scanning electron microscope images of sequential exposed surfaces of a sample generated as described above. FIG. 3O is an image illustrating the computed difference between the sequential images of FIGS. 3M and 3N. The results shown in FIGS. 3F, 3I, 3L, and 3O are comparable to those shown in FIG. 3C and described above.

Figure 4A:
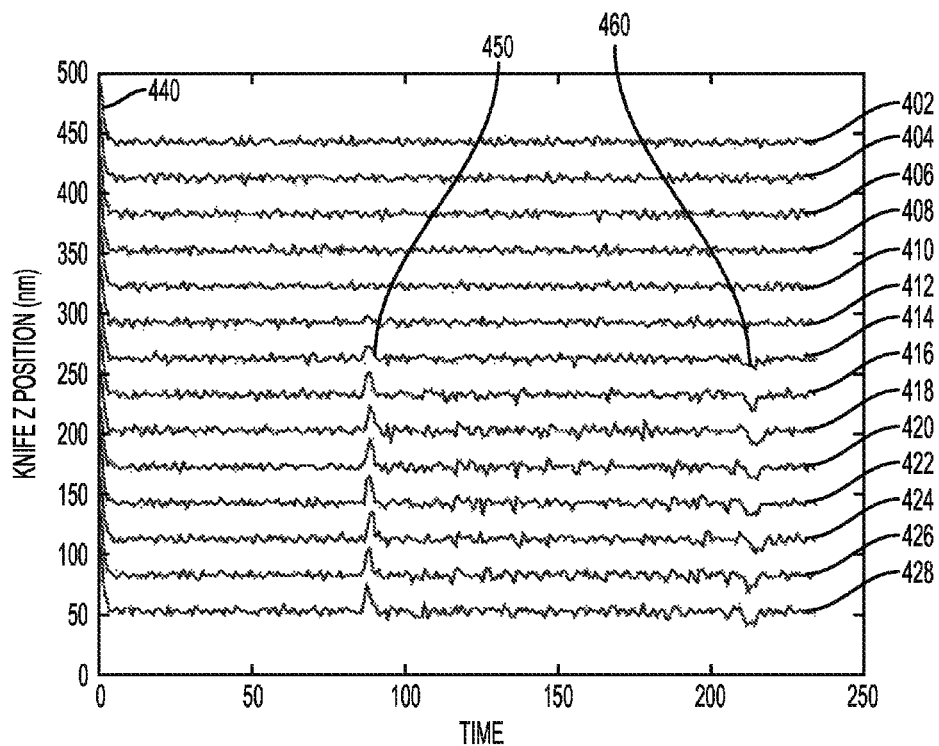
FIG. 4A is a graph showing output from a capacitive sensor measuring the vertical position of a knife blade of a microtome, as a tissue sample is moved across the knife blade several times.
Figure 4B:
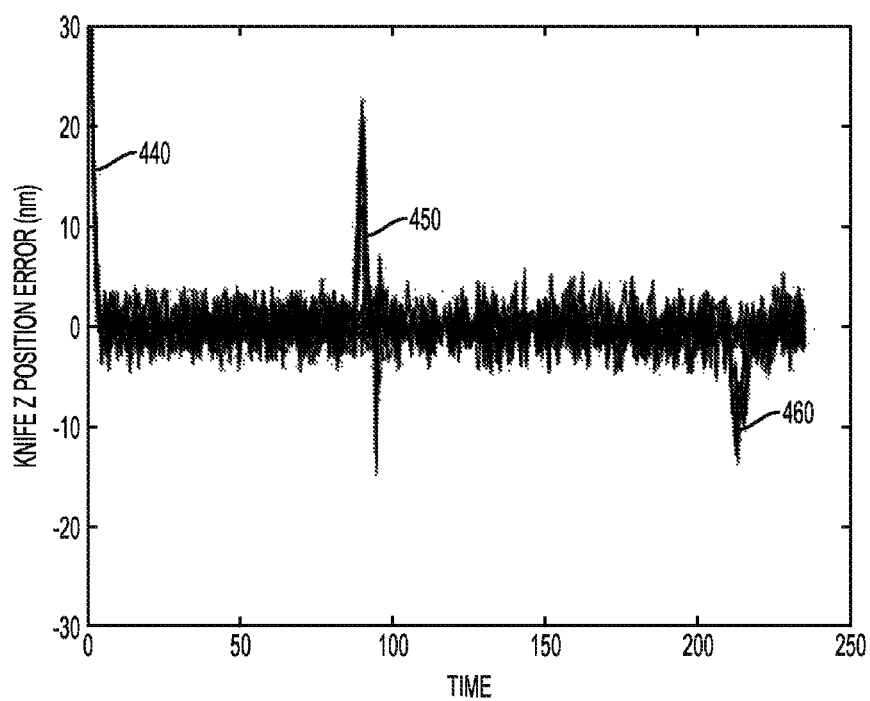
FIG. 4B is a graph showing the data series of FIG. 4A overlaying one another.

FIG. 4A is a graph showing output, in a plurality of data series, from the capacitive sensor described above, measuring the vertical position of the microtome blade as a tissue sample is moved across the blade fourteen times. FIG. 4B is a graph showing the data series of FIG. 4A overlaying one another. As shown in FIGS. 4A-4B, the y-axis of the graphs illustrates the height of the blade, and the x-axis of the graphs illustrates increments of time as the sample is moved across the blade. With reference to data series 402 of FIG. 4A, it can be seen at 440 that the blade is initially lowered to a desired location. Once the blade is positioned as desired, the sample can be moved across the blade. The data presented in FIG. 4A reveals that in the first six times the sample was moved across the blade, as shown in data series 402, 404, 406, 408, 410, and 412, the sample did not come into contact with the blade.

With reference to data series 414 of FIG. 4A, it can be seen at 450 that the sample contacted the blade as it moved across. The initiation of contact between the sample and the blade results in the blade being pushed up, before the feedback loop has an opportunity to correct and bring the blade back down to the desired location. With further reference to data series 414 of FIG. 4A, it can be seen that the sample ceases to be in contact with the blade at 460. The cessation of contact between the sample and the blade results in the blade dropping off the end of the sample before the feedback loop has an opportunity to correct and bring the blade back up to the desired location. The characteristic pattern of the blade being pushed up at the initiation of contact, the feedback loop correcting to move the blade down, the blade dropping down at the cessation of contact, and the feedback loop correcting to move the blade up, can be seen throughout the remaining data series 416, 418, 420, 422, 424, 426, and 428.

This data provides a distinct advantage over that obtained with prior microtomes. For example, in known microtomes, there is no simple method for precisely determining the location of the blade with respect to the sample. Thus, in many cases, preparation of a microtome for use in SBEM applications requires that the researcher image the surface of the sample, move the blade across the sample, image the surface of the sample again, and compare the two images to determine whether any portion of the sample was removed. If no portion was removed, the blade would be moved a small distance closer to the sample, and the process would be repeated. This process would be iterated until, by comparing successive images, it was determined that a portion of the sample had been removed. This process can be highly time-consuming and inefficient, as well as error-prone, and would have to be performed often, as any extended period of non-use of the microtome could render the precise relative locations of the blade and the sample unknown. Further, this process introduces a large electron dose to the sample, which can change the material properties of the plastic coating (e.g., by breaking bonds in the plastic polymer) thus making slicing the sample more difficult and leading to chatter and/or less consistent section thicknesses. Thus, the microtomes described herein provide more efficient and effective methods of calibration and interruption recovery.

FIG. 4B, illustrating the data series of FIG. 4A overlaying one another, illustrates the consistency of the data series and thus the consistency of the performance of the microtome as it removes a series of portions from the surface of a sample.

Figure 5:
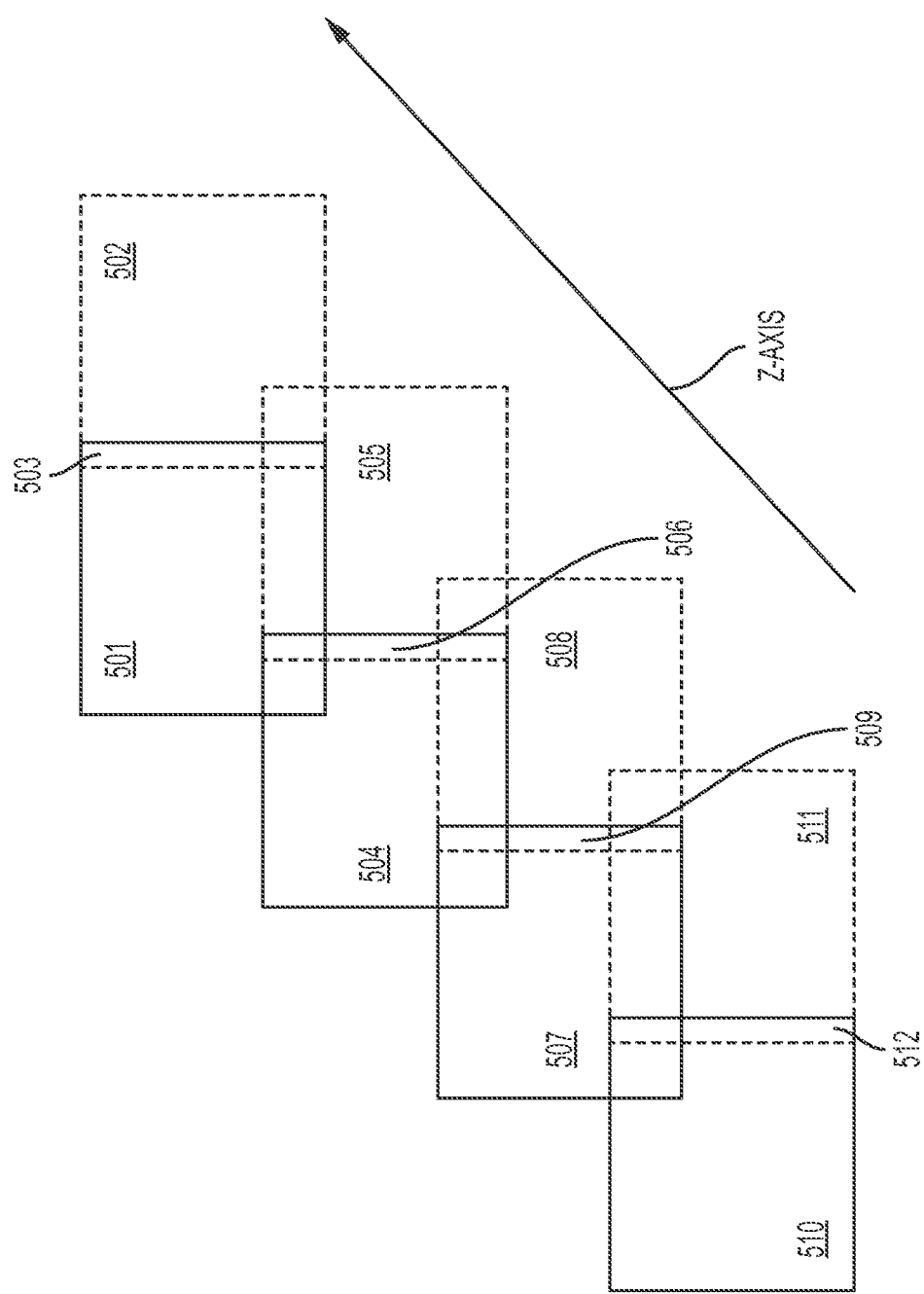
FIG. 5 is a diagram showing the locations of a plurality of constituent scanning electron microscope images.

In some cases, a scanning electron microscope is capable of imaging a region of a surface no larger than 50 microns by 50 microns. Samples to be studied using SBEM techniques, however, can often have sizes in the range of 500 microns by 500 microns. Thus, in some cases, multiple scanning electron microscope images taken on the same plane are stitched together to create a larger composite image of the surface of a sample. For example, as shown in FIG. 5, a scanning electron microscope can be used to take a first image of a first area 501 of an exposed surface of a sample at a first location. The built-in stage of the scanning electron microscope is then used to translate the sample from the first location to a second location, and the scanning electron microscope can be used to take a second image of a second area 502. The two images can then be stitched together, for example, using post-processing software. In some cases, the area of the sample shown in the first image can have a region that overlaps the area of the sample shown in the second image, and the overlap region 503 can be used by the post-processing software to stitch the two images together to form the composite image.

Once the two images have been taken, the top portion of the sample can be removed as described above, the sample can be returned to its first position, and the process can be repeated for the newly exposed surface by imaging first area 504 and second area 505 having overlap region 506. This process can be repeated for first area 507, second area 508, and overlap region 509 of a third exposed surface, and for first area 510, second area 511, and overlap region 512 of a fourth exposed surface.

In order for such a technique to be effectively combined with an SBEM process, the stage preferably has precision sufficient to ensure that the sample comes to rest in the same locations for the imaging of each successive exposed surface. Further, the overlap region 503 between the first area 501 and the second area 502 preferably is large enough to ensure that, given some error in the translation of the microtome, at least some overlap region exists to allow the first and second images to be stitched together. Thus, a more precise stage can allow for a smaller overlap area and therefore a larger composite image. Based on the built-in stages of typical scanning electron microscopes, an overlap region of about 1 micrometer has been found to be sufficient in many cases.

It has been found that the built-in stage of the FEI NanoSEM 450 scanning electron microscope has sufficient precision for these purposes. If the built-in stage of a scanning electron microscope is found to be insufficiently precise, however, an intermediate linear translation stage can be mounted on the built-in stage, and the microtome can be mounted on the intermediate stage. One suitable intermediate stage is the P-625.2 XY Piezo Stage, commercially available from Physik Instrument. In this case, the built-in stage can provide coarse adjustment and the intermediate stage can provide fine adjustment.

Figure 6A:
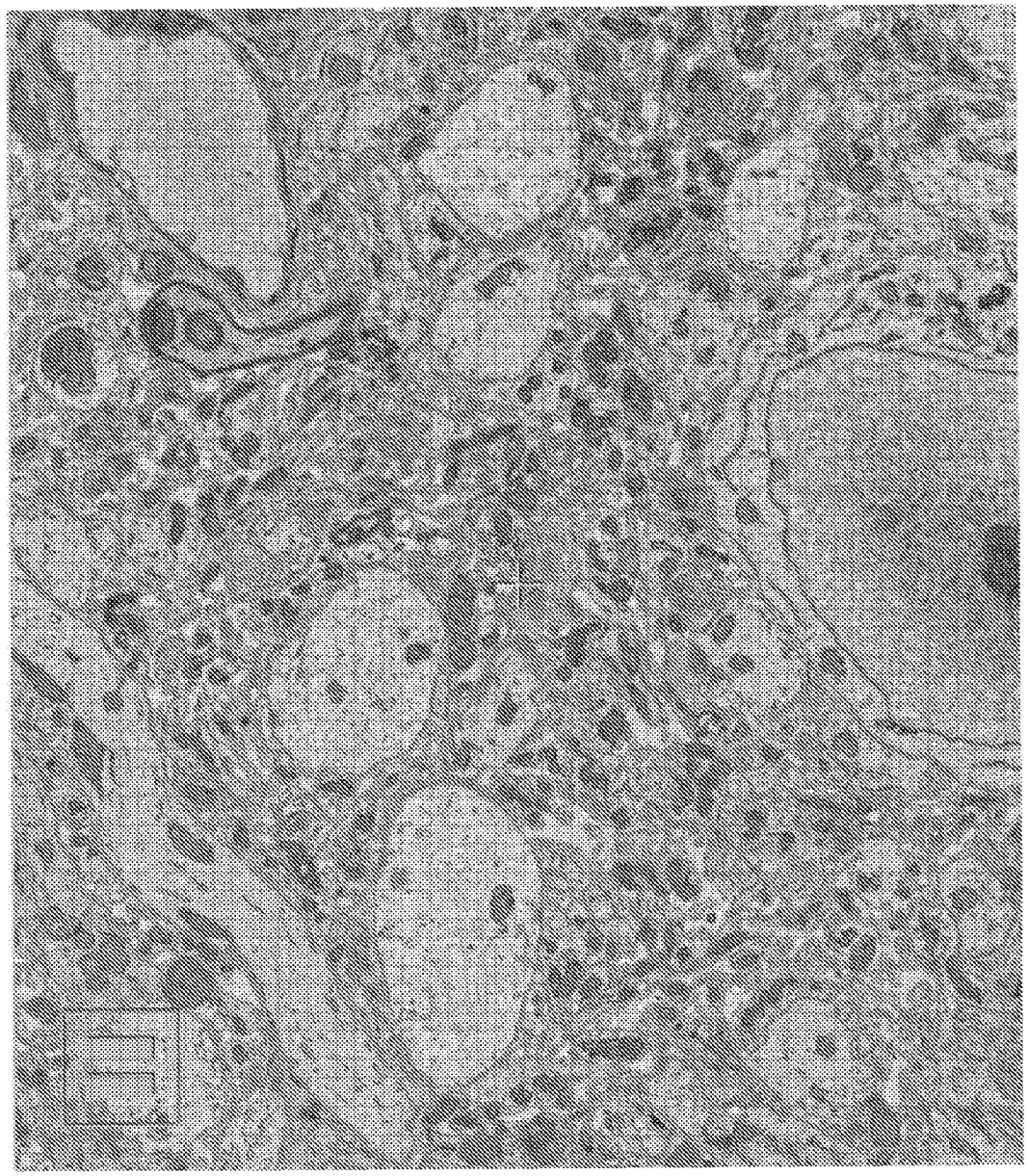
FIGS. 6A-6C are scanning electron microscope images taken of the same sample at different working distances.
Figure 6B:
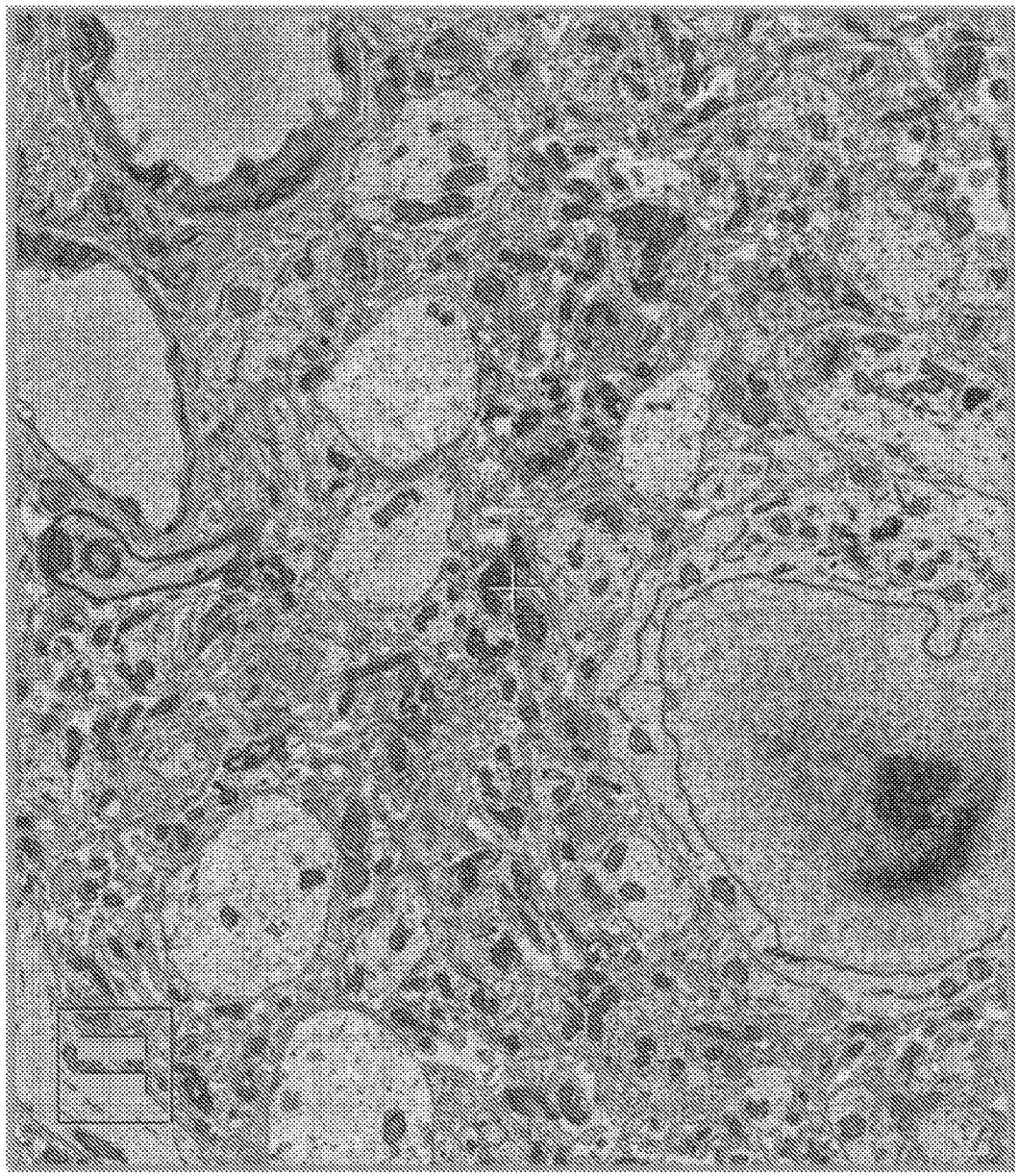
Figure 6C:
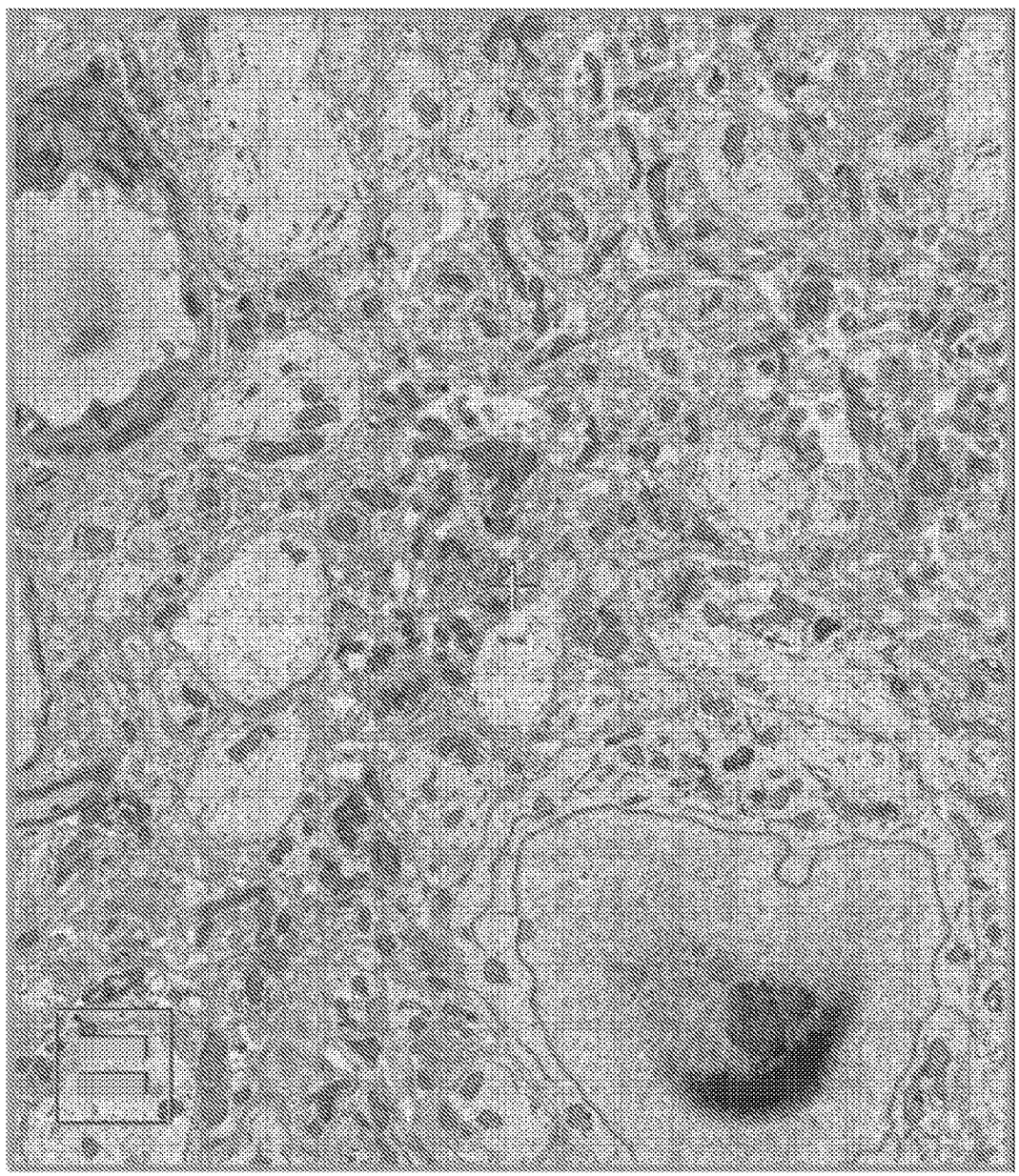

FIG. 6A is a scanning electron microscope image of a tissue sample, taken at a working distance of 3.1 mm. FIG. 6B is a scanning electron microscope image of the same tissue sample, taken at a working distance of 4.0 mm. FIG. 6C is a scanning electron microscope image of the same tissue sample, taken at a working distance of 4.9 mm. Taken together, the images shown in FIGS. 6A-6C illustrate that by decreasing the working distance, higher signal-to-noise ratio images of the tissue sample can be obtained. This illustrates one advantage of the microtomes described above, in that they can allow scanning electron microscope images to be taken at shorter working distances than prior microtomes can.

In a typical scanning electron microscope, an electron beam can be provided with an accelerating voltage of 2 kV and the sample is grounded as described above. In this case, the electrons collected by the detector have almost 2 kV, or in some cases about 1.9 kV. FIG. 7 illustrates an alternative microtome 700, in which a voltage is applied to the sample 702. This can be achieved by electrically isolating the sample 702 from the pedestal 704 and applying a voltage to the sample 702, for example, through the gold coating applied thereto. This can also be achieved by providing an insulator 706 to electrically isolate the pedestal 704, and applying a voltage to the pedestal 704, for example, by applying the voltage at 708. In this case, the application of the voltage to the pedestal 704 results in electric field lines 710.

FIG. 7 illustrates an electron beam 712 exiting the pole piece of a scanning electron microscope and being directed along the beam axis of the scanning electron microscope to the charged sample 702, and a detector 714 collecting secondary and backscattered electrons from the sample 702. In one specific embodiment, the electron beam 712 can be provided with an accelerating voltage of 6 kV and the sample 702 can be provided with a −4 kV voltage. In this scenario, the electron beam 712 collides with the sample 702 with the same energy (2 kV) as in the grounded-sample case described above due to beam deceleration, but the electrons collected by the detector 714 have an energy approaching 6 kV, or in some cases about 5.9 kV, due to beam acceleration, and a greater number of electrons are directed back to the detector 714. Thus, the data collected by the embodiment shown in FIG. 7 can be higher quality, and can have an improved signal-to-noise ratio.

In some embodiments, electron tomography can be used to improve results. Electron tomography is a technique in which an electron beam is directed to a sample at various degrees of rotation about its center. FIGS. 8A-8C show different configurations of a microtome 800 and detector 802 of a scanning electron microscope suitable for use in electron tomography applications. FIG. 8A shows the microtome 800 at 0° tilt and the detector 802 located above the sample 804. FIG. 8B shows the microtome 800 at 20° tilt and the detector 802 located above the sample 804. FIG. 8C shows the microtome 800 at 20° tilt and the detector 802 located to the side of the sample 804 to increase electron detection efficiency. 20° is illustrated as an exemplary angle of tilt and in practice the angle can vary over a wide range of suitable angles.

The collection of the resulting electrons allows a reconstruction of detailed three-dimensional structures of the sample 804. One advantage of this technique is that it can allow more detailed study of the three dimensional structure of the sample 804, or it can allow a similarly detailed study with a less precise microtome (because the slices of material removed from the surface of the sample 804 need not be as thin). Because this technique requires the ability to rotate the sample 804, it cannot be employed in combination with known microtomes which do not allow rotation of the sample 804. With regard to the microtomes described herein, rotation of the sample 804 can be effected either by rotation of the scanning electron microscope's stage (and thus the entire microtome 800), or by the rotation of the pedestal about the pivot bearing.

FIGS. 9A-9E show another exemplary microtome 900. The microtome 900 includes many of the components described above with respect to microtome 100. Microtome 900 includes a vertical flexure element 902 which couples blade support 904 to linear actuator 906. The vertical flexure element 902 is advantageous because it minimizes the vertical motion of the blade 908 as it oscillates back and forth. Microtome 900 also includes an insulator 910 to electrically isolate the sample 914. The insulator 910 can be fabricated from polyether ether ketone (PEEK), or other vacuum-compatible material. Microtome 900 also includes a slot 912 within which a Styrofoam cleaning rod (not illustrated) is situated to allow the blade 908 to be cleaned after cutting the sample 914. Microtome 900 also includes a heat sink 916. The heat sink 916 provides additional heat dissipation from the linear actuator 140 when it is used in a vacuum chamber.

Figure 9A:
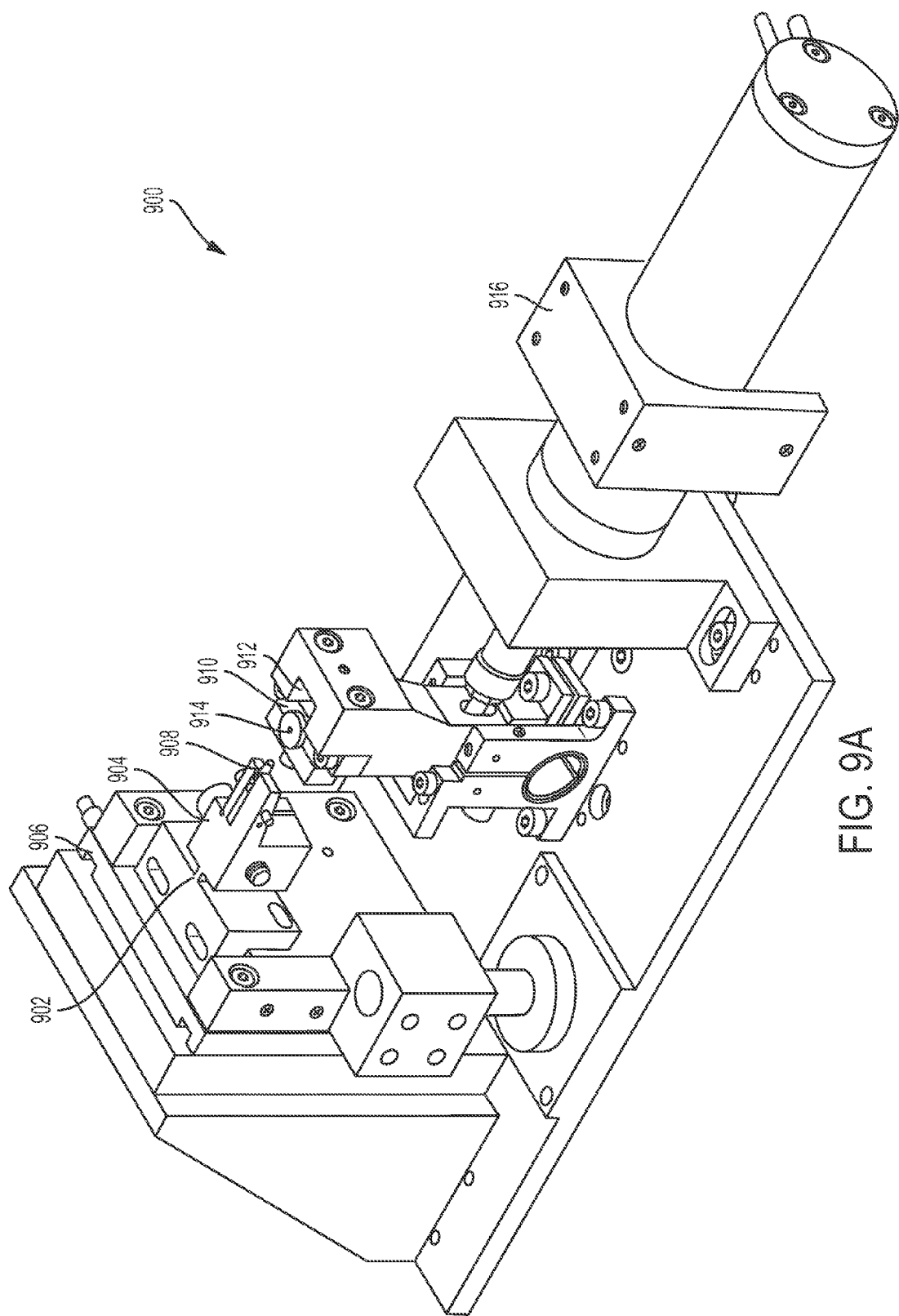
FIGS. 9A-9E are different views of another exemplary microtome.
Figure 9B:
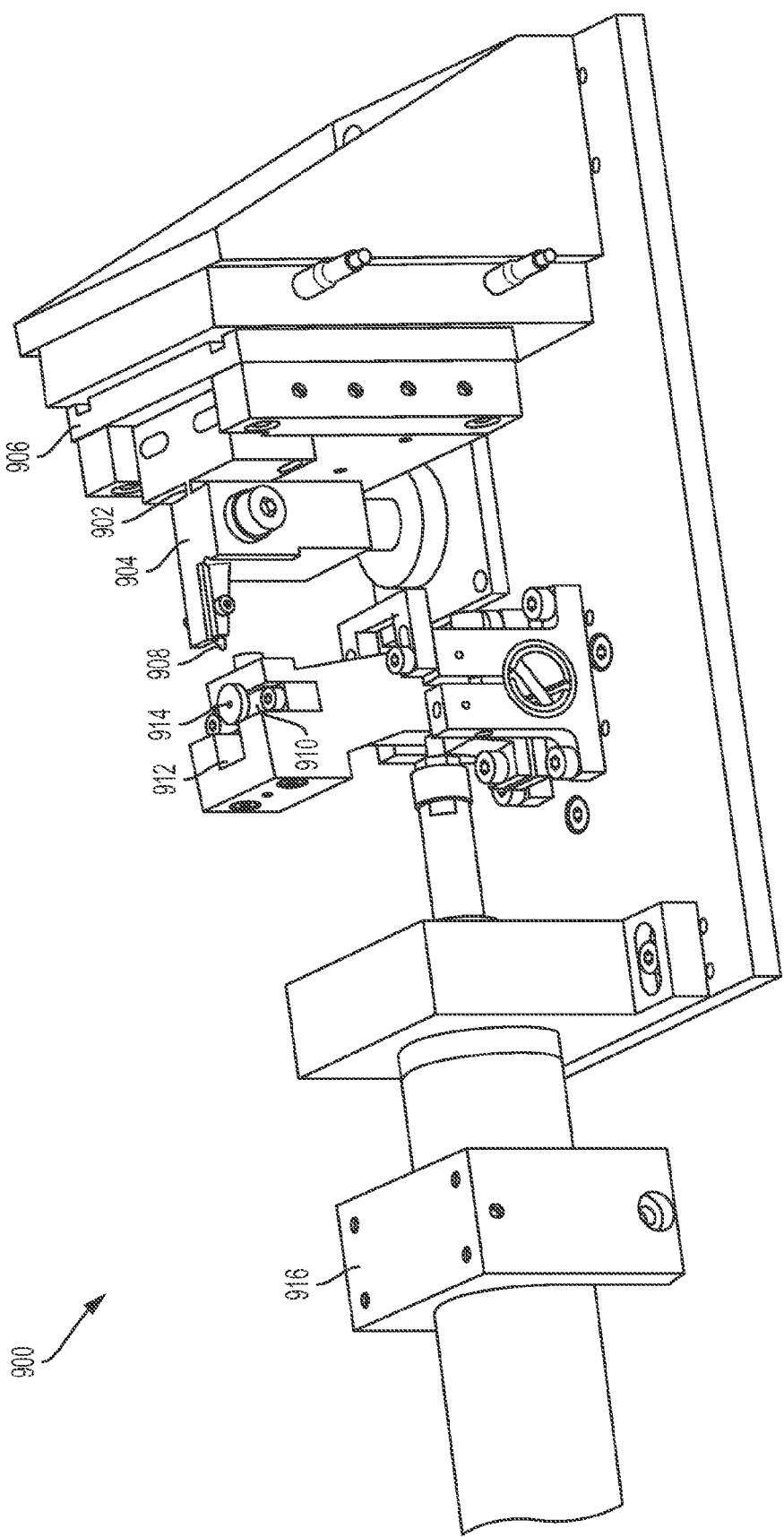
Figure 9C:
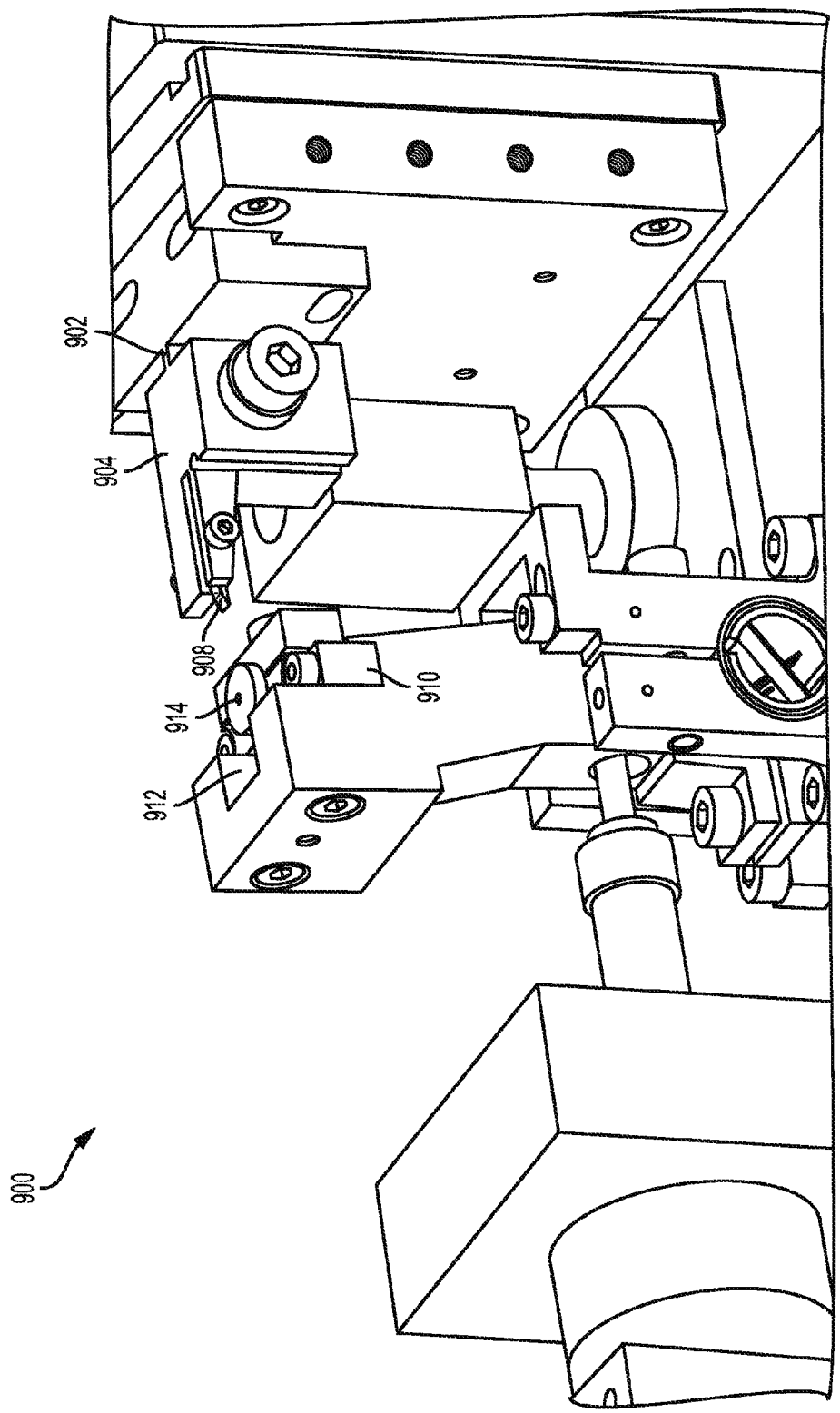
Figure 9D:
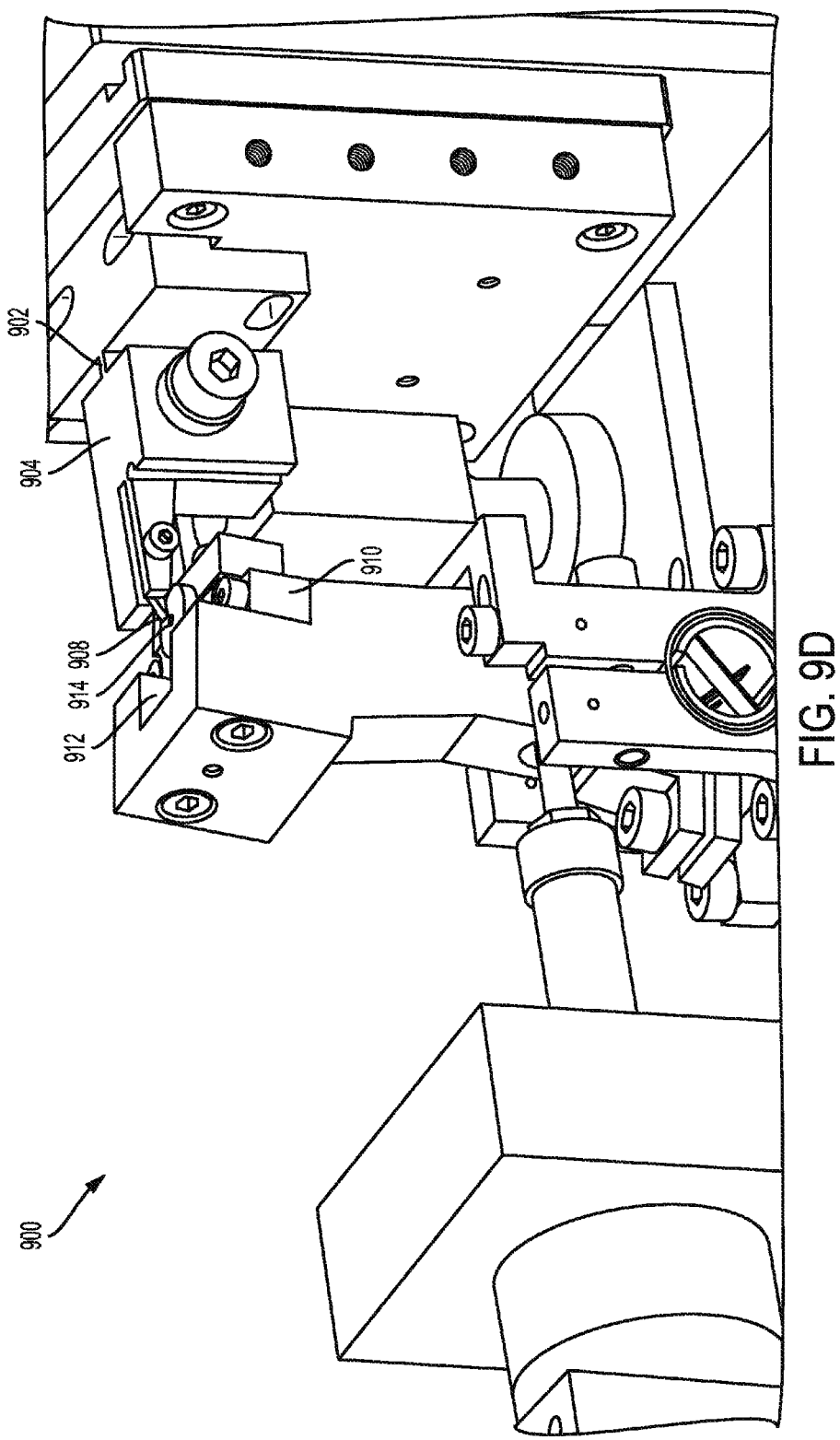
Figure 9E:
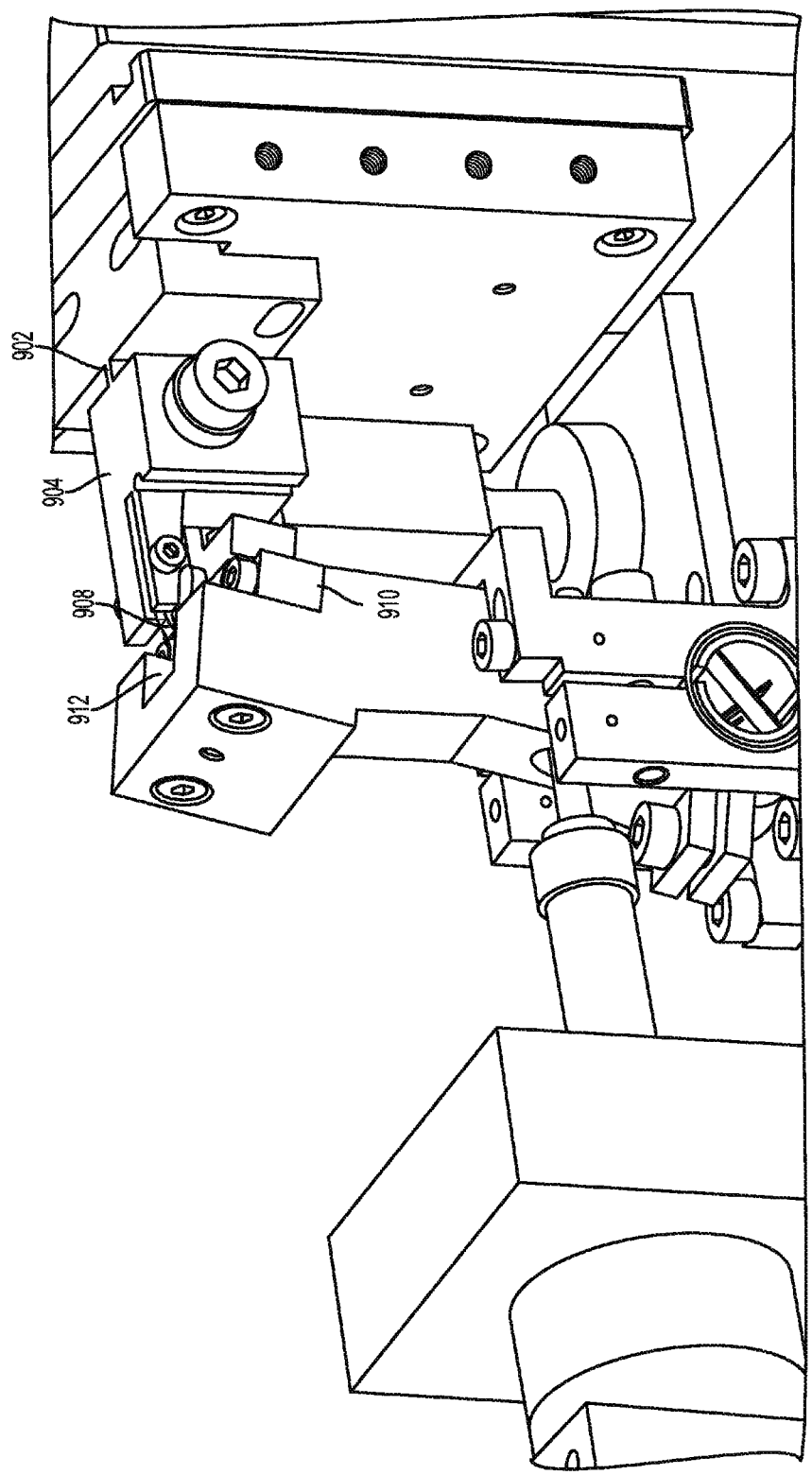

FIG. 9B illustrates the microtome 900 from an alternative angle. FIG. 9C illustrates the microtome 900 in an imaging configuration wherein the sample is situated under an electron beam of a scanning electron microscope. FIG. 9D illustrates the microtome 900 in a cutting configuration wherein the blade 908 is cutting the sample 914. FIG. 9E illustrates the microtome 900 in a cleaning configuration wherein the blade 908 can be cleaned with a Styrofoam cleaning rod in the slot 912.

FIGS. 10A and 10B are scanning electron microscope images of exposed surfaces of a tissue sample generated during serial block-face scanning electron microscopy using a microtome as described herein to remove a slice of thickness 15 nanometers from a sample. FIG. 10A shows an XY view through a stack of data, while FIG. 10B shows an XZ view through a stack of data.

Figure 11:
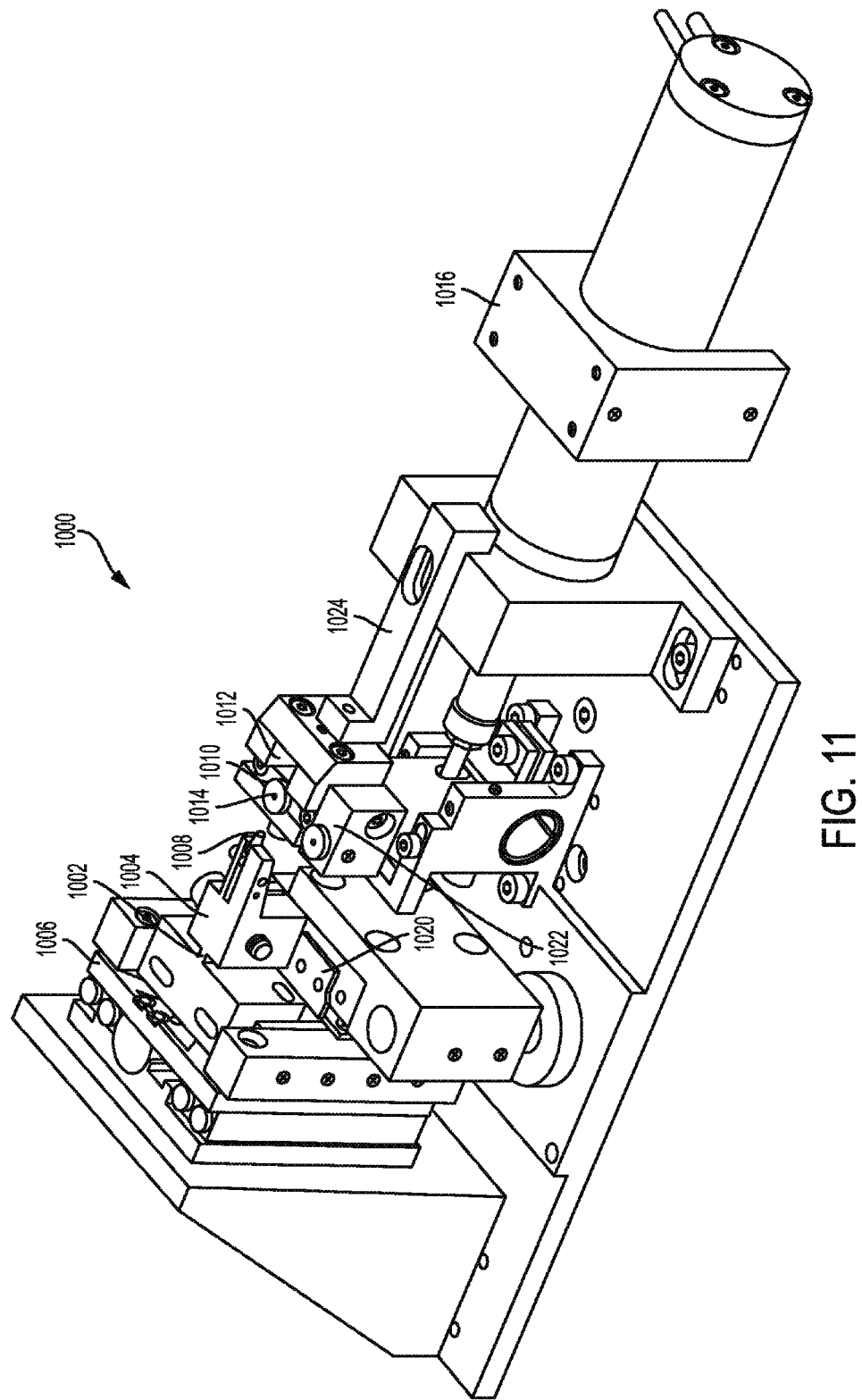
FIG. 11 is a perspective view of yet another exemplary microtome.

FIG. 11 shows another exemplary microtome 1000. The microtome 1000 includes many of the components described above with respect to microtome 900. Microtome 1000 includes a vertical flexure element 1002 which couples blade support 1004 to linear actuator 1006. The vertical flexure element 1002 is advantageous because it minimizes the vertical motion of the blade 1008 as it oscillates back and forth. Microtome 1000 also includes an insulator 1010 to electrically isolate the sample 1014. The insulator 1010 can be fabricated from polyether ether ketone (PEEK), or other vacuum-compatible material. Microtome 1000 also includes a slot 1012 within which a Styrofoam cleaning rod (not illustrated) can be situated to allow the blade 1008 to be cleaned after cutting the sample 1014. Microtome 1000 also includes a heat sink 1016. The heat sink 1016 provides additional heat dissipation from the linear actuator when it is used in a vacuum chamber.

The microtome 1000 can also include a linear stage, or piezo stage, 1020 to reset the capacitive sensor to the top of its range. The capacitive sensor can have a range of about 600 microns. After cutting through 600 microns of tissue, the linear stage 1020 can raise the sensor to the top of the capacitive sensor range without changing the position of the knife 1008 relative to the sample 1014. This effectively increases the cutting range along the Z axis from 600 microns to the range of the linear stage 1020 (e.g., to about 25 mm).

The microtome 1000 can also include a polymeric mount 1022 positioned next to the sample 1014 on which a Faraday cup can be installed or held. The addition of the mount 1022 can allow the electron beam current to be monitored by occasionally translating a Faraday cup under the electron beam using the SEM stage.

The microtome 1000 can also include a clamp 1024 to hold the pedestal still while mounting samples (e.g., so the pedestal does not unintentionally pivot while mounting a sample). The clamp 1024 can be removed once data collection begins.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an", and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A", "B,", "C", "A and B", "A and C", "B and C", or "A, B, and C."

As used herein, the term "coupled" generally means physically, magnetically, chemically, electrically, or otherwise coupled or linked and does not exclude the presence of intermediate elements between the coupled elements absent specific contrary language.

In view of the many possible embodiments to which the principles disclosed herein may be applied, it should be recognized that illustrated embodiments are only examples and should not be considered a limitation on the scope of the disclosure. Rather, the scope of the disclosure is at least as broad as the invention(s) defined by the following claims. I therefore claim as my invention all that comes within the scope of these claims.

I claim:

1. A microtome for removing a thin portion of the top of a sample, the microtome comprising:
    a base plate;
    a pedestal coupled to the base plate such that the pedestal can be moved from an imaging location to a cutting location, wherein the pedestal has an exposed surface on which the sample can be mounted; and
    a blade coupled to the base plate such that a blade location with respect to the base plate can be adjusted by moving the blade in a direction perpendicular to the exposed surface of the pedestal when the pedestal is in the imaging location, to selectively vary a distance between the blade and the base plate;
    wherein the cutting location is closer to the blade than the imaging location.

2. The microtome of claim 1, wherein the microtome is mounted on a fluorescence microscope configured to image a surface of the sample using a camera.

3. The microtome of claim 1, wherein the microtome is mounted on a cathodoluminescence microscope configured to image a surface of the sample using a camera.

4. The microtome of claim 1, wherein the microtome is mounted on a photoemission electron microscope configured to image a surface of the sample using a camera.

5. The microtome of claim 1, wherein the blade is mounted on a first computer-controlled linear actuator coupled to the base plate.

6. The microtome of claim 5, wherein the pedestal is mounted on a lever coupled to the base plate by a pivot bearing.

7. The microtome of claim 6, wherein the pedestal can be rotated about the pivot bearing by actuation of a second computer-controlled linear actuator coupled to the base plate.

8. The microtome of claim 7, wherein the first actuator is configured to receive a control signal to direct movement of the blade, the microtome further comprising:

a sensor coupled to the first actuator and configured to produce an output signal indicating the blade location with respect to the base plate; and a computer program configured to receive the output signal from the sensor, generate the control signal based at least in part on the output signal from the sensor, and transmit the control signal to the first actuator.

9. The microtome of claim 1, further comprising a sample positioned on the pedestal.

10. The microtome of claim 9, wherein a working distance between the sample and a pole piece of the scanning electron microscope can be selected from a range of available working distances.

11. The microtome of claim 9, wherein a voltage is applied to the sample.

12. The microtome of claim 11, wherein the sample is electrically isolated from the microtome.

13. The microtome of claim 1, wherein the blade is a piezo-electrically controlled oscillating diamond blade.

14. The microtome of claim 1, further comprising a computing apparatus including a processor and memory, the memory storing computer readable instructions for combining a plurality of images of the sample to create a three-dimensional representation of the sample.

15. The microtome of claim 1, further comprising a linear piezo stage configured to reset a capacitive sensor without changing a position of the blade relative to the base plate.

16. The microtome of claim 1, further comprising a polymeric mount coupled to the pedestal and configured to hold a Faraday cup.

17. The microtome of claim 1, further comprising a clamp coupled to the pedestal and the base plate and configured to hold the pedestal still relative to the base plate while a sample is mounted to the pedestal.

18. A microtome configured to be installed within a scanning electron microscope, comprising:

a blade coupled to an actuator, wherein the actuator is coupled to a stage of the scanning electron microscope such that the actuator can move the blade with respect to the stage in a direction parallel to a beam axis of the scanning electron microscope, and wherein the actuator is configured to receive a control signal to direct movement of the blade;

a sensor coupled to the actuator and configured to produce an output signal indicating the blade location with respect to the base plate; and a computer program configured to receive the output signal from the sensor, generate a control signal based at least in part on the output signal from the sensor, and transmit the control signal to the actuator.

19. The microtome of claim 18, further comprising a pedestal coupled to the stage such that the pedestal can be moved from an imaging location on the beam axis to a cutting location off the beam axis, wherein the cutting location is closer to the blade than the imaging location.

20. A method comprising:

positioning a sample at an imaging location on a microtome within a scanning electron microscope, wherein the imaging location is on a beam axis of the scanning electron microscope;

imaging a first exposed surface of the sample;

setting a height of a blade of the microtome;

moving the sample from the imaging location to a cutting location, wherein the cutting location is closer to the blade than the imaging location and not on the beam axis;

moving the sample across the blade to remove a portion of the sample and reveal a second exposed surface of the sample;

moving the sample to the imaging location; and imaging the second exposed surface of the sample.

21. The method of claim 20, further comprising, after setting the height of the blade, maintaining the height of the blade under feedback control.

22. The method of claim 20, further comprising, prior to imaging the second exposed surface, focusing an electron beam of the scanning electron microscope at the second exposed surface.

23. The method of claim 20, further comprising, prior to imaging the second exposed surface, adjusting the sample along the beam axis.

24. The method of claim 23, further comprising, after adjusting the sample along the beam axis, focusing an electron beam of the scanning electron microscope at the second exposed surface.

25. The method of claim 20, wherein the act of imaging the first exposed surface of the sample comprises:

using the scanning electron microscope to capture a plurality of constituent images of the first exposed surface; and stitching the plurality of constituent images together to form a composite image of the first exposed surface.

26. The method of claim 20, wherein the method further comprises tilting the microtome such that the beam axis is not perpendicular to the exposed surface of the sample.

27. The method of claim 20, wherein the method further comprises rotating the microtome.

28. The method of claim 20, wherein the method further comprises cleaning the blade with a styrofoam cleaning rod.

29. The method of claim 20, wherein the microtome is mounted on an intermediate stage and the intermediate stage is mounted on a built-in stage of the scanning electron microscope.

30. The method of claim 20, further comprising resetting a capacitive sensor without changing a position of the knife relative to the sample.

31. The method of claim 20, further comprising mounting a Faraday cup to a polymeric mount coupled to the pedestal.

32. The method of claim 20, further comprising securing a clamp between the pedestal and the base plate to hold the pedestal still relative to the base plate while a sample is mounted to the pedestal.

* * * * *